United States Patent [19]

Nakagami et al.

[11] 4,213,987
[45] Jul. 22, 1980

[54] AGRICULTURAL FUNGICIDAL METHOD

[75] Inventors: Kazuto Nakagami; Shinji Yokoi, both of Yasumachi; Kenji Nishimura, Ube; Shigeki Nagai, Ube; Takeo Honda, Ube; Kiroku Oda, Ube; Katsutoshi Fujii, Ube; Ryuji Kobayashi, Ube; Mikio Kojima, Ube, all of Japan

[73] Assignees: Sankyo Company Limited, Tokyo; Ube Industries, Ltd., Ube, both of Japan

[21] Appl. No.: 910,117

[22] Filed: May 30, 1978

[30] Foreign Application Priority Data

Jun. 7, 1977 [JP] Japan ................................ 52-67034

[51] Int. Cl.$^2$ ............................................. A01N 9/22
[52] U.S. Cl. ...................................... 424/251; 544/293
[58] Field of Search ........................... 544/293; 424/251

[56] References Cited

U.S. PATENT DOCUMENTS

| 3,541,094 | 11/1970 | Lutz et al. | 424/251 X |
| 3,560,619 | 2/1971 | Harrison et al. | 424/251 |
| 3,574,210 | 4/1971 | Breuer et al. | 424/251 |
| 3,594,480 | 7/1971 | Cronin et al. | 424/251 X |

FOREIGN PATENT DOCUMENTS

| 1528020 | 4/1967 | France | 424/251 |
| 38-11148 | 7/1963 | Japan | 424/251 |
| 446506 | 1/1976 | U.S.S.R. | 544/293 |

OTHER PUBLICATIONS

Christensen et al., J.A.C.S., 7/1946, vol. 68, pp. 1306–1308.

Primary Examiner—Dale R. Ore
Attorney, Agent, or Firm—Frishauf, Holtz, Goodman & Woodward

[57] ABSTRACT

Agricultural fungicidal compositions containing as an active ingredient one or more 4-aminoquinazoline derivatives. The amino group is substituted, e.g., with a phenoxyalkylene, and the quinazoline nucleus may be substituted at 2- and or 6-positions.

33 Claims, No Drawings

AGRICULTURAL FUNGICIDAL METHOD

The invention relates to agricultural fungicidal compositions containing as an active ingredient one or more 4-aminoquinazoline derivatives.

More particularly, it relates to agricultural fungicidal compositions containing as an active ingredient one or more 4-aminoquinazoline derivatives represented by formula (I):

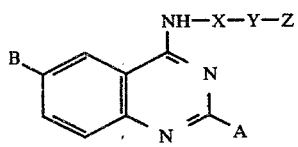

in which:

A and B are the same or different and each represents a hydrogen atom, a lower alkyl group, a halogen atom or a nitro group;

X represents an alkylene group;

Y represents an oxygen atom or a sulfur atom;

Z represents an alkyl group, an aralkyl group; a naphthyl group, an unsubstituted phenyl group or a phenyl group substituted with 1 to 3 substituents which are the same or different and are selected from the group consisting of a lower alkyl group, an alkoxy group, an alkylthio group, a phenyl group, a trifluoromethyl group and a halogen atom; or salts thereof.

A class of 4-aminoquinazoline derivatives is disclosed in Japanese Patent Publication Specification No. 43-29033, which corresponds to U.S. Pat. No. 3,541,094 as being effective controlling agents against phytopathogenic fungi.

The inventors have found that the compounds of formula (I) show a broad and superior fungicidal activity than the known compounds mentioned above against bacteria and fungi parasitic on agricultural and horticultural plants. More specifically, the compounds of formula (I) show a remarkable controlling effect against, for example, blast, brown spot, sheath blight and bacterial leaf blight of rice plants; late blight and early blight of tomatoes; and anthracnose, downy mildew and powdery mildew of cucumbers. They also show a controlling effect against phytoparasitic soil fungi, as well as algal fungi which adversely affect the germination of rice plants.

Further, some of the compounds of formula (I) show a strong inhibiting activity of ingestion against the fourth to final instar larvae of Lepidoptera such as cabbage armyworm and tobacco cutworm, and therefore are useful as an insect repellent. Furthermore, some of the compounds of formula (I) may be used as an insecticidal and acaricidal agent gainst, e.g., two-spotted spider mite.

In the compounds of formula (I), when A and/or B each represents a lower alkyl group, it may be a straight or branched chain alkyl having 1 to 4 carbon atoms, for example, a methyl, ethyl, n-propyl, isopropyl, n-butyl or sec-butyl, preferably a methyl.

When A and/or B each represents a halogen atom, it may be, for example, a chlorine, bromine, fluorine or iodine, preferably a chlorine.

X is a straight or branched alkylene and it may be, for example, a methylene, ethylene, methylmethylene, trimethylene, ethylmethylene, dimethylmethylene, propylene, tetramethylene, 1,1-dimethylethylene, 1,2-dimethylethylene, 2,2-dimethylethylene, 1-ethylethylene, 2-ethylethylene, pentamethylene, hexamethylene, heptamethylene, octamethylene, 2-ethylhexamethylene, 5-ethylhexamethylene, decamethylene, dodecamethylene, hexadecamethylene or octadecamethylene; and it is preferably a straight or branched chain alkylene having 2 to 8 carbon atoms.

When Z is an alkyl group, it may be, for example a methyl, ethyl, n-propyl, isopropyl, n-butyl, isobutyl, sec-butyl, tert-butyl, n-amyl, isoamyl, sec-amyl, n-heptyl, n-octyl, 2-ethylhexyl, decyl, dodecyl, tetradecyl, hexadecyl or octadecyl; and it is preferably a straight or branched alkyl having 1 to 8 carbon atoms.

When Z is a naphthyl group, it may be a 1-naphthyl or 2-naphthyl.

When Z is an aralkyl group, it may be, for example, a benzyl, α-methylbenzyl or phenethyl, preferably a benzyl.

When Z is a phenyl group substituted with lower alkyl, the lower alkyl may be straight or branched chain alkyl having 1 to 4 carbon atoms such as methyl, ethyl, n-propyl iscpropyl, n-butyl or sec-butyl, preferably methyl.

When Z is a phenyl group substituted with lower alkoxy, the lower alkoxy may be straight or branched chain alkoxy having 1 to 4 carbon atoms such as methoxy, ethoxy, n-propoxy, isopropoxy, n-butoxy or isobutoxy, preferably methoxy or ethoxy.

When Z is a phenyl group substituted with lower alkylthio, the lower alkylthio may be straight or branched chain alkylthio having 1 to 4 carbon atoms such as methylthio, ethylthio, n-propylthio, isopropylthio, n-butylthio or isobutylthio, preferably methyl thio.

When Z is a phenyl group substituted with halogen atom, the halogen atom may be chlorine, bromine, fluorine or iodine, preferably chlorine.

Of the compounds of formula (I), the preferable class of compounds is when A is a hydrogen atom or a chlorine atom; B is a hydrogen atom, a methyl group, a chlorine atom or a nitro group; X is a straight or branched alkylene group having from 2 to 8 carbon atoms; and Z is an unsubstituted phenyl group or a phenyl group substituted with 1 to 3 substituents which are the same or different and are selected from the group consisting of a methyl, methoxy, ethoxy, methylthio, trifluoromethyl and chlorine.

Among the preferable compounds mentioned above, the more preferable class of compounds is when both A and B are hydrogen atoms; X is a straight or branched chain alkylene group having 2 to 8 carbon atoms; and Z is an unsubstituted phenyl group or a phenyl group substituted with a methyl, methoxy, ethoxy or chlorine.

The most preferable class of compounds is when both A and B are hydrogen atoms; X is a straight or branched alkylene group having 2 to 8 carbon atoms; Y is an oxygen atom; and Z is an unsubstituted phenyl group or a phenyl group substituted with a methyl, methoxy, ethoxy or chlorine.

As can be understood by formula (I), the compounds of the invention have at least one asymmetric carbon atom, depending on the species of the alkylene group X. In such cases, there can be present various different optical isomers. It is, therefore, to be understood that the individual stereoisomers as well as physical or racemic mixtures thereof are included within the scope of the invention.

The compounds of formula (I) may readily form acid addition salts; and such salts may also be used as the active ingredient of the agricultural fungicides of the invention.

Acids to form addition salts include: inorganic acids such as hydrochloric acid, hydrobromic acid, nitric acid, sulfuric acid and phosphoric acid; carboxylic acids such as formic acid, oxalic acid and trichloroacetic acid; and organic sulfonic acids such as methanesulfonic acid, benzenesulfonic acid and toluenesulfonic acid. Thereof, hydrochloric acid is preferable.

Further, the compounds of formula (I) may form hydrates with water; and the hydrates may also be used as the active ingredient of the agricultural fungicides of the invention.

The compounds of formula (I) used as the active ingredient of the fungicides of the invention will be illustrated below. The numbers appended to the compounds will be used to identify them hereafter.

1. 4-(2-Methoxyethyl)aminoquinazoline
2. 4-(2-Ethoxyethyl)aminoquinazoline
3. 4-(2-Ethylthioethyl)aminoquinazoline
4. 2-Chloro-4-(2-ethoxyethyl)aminoquinazoline
5. 2-Chloro-4-(2-ethylthioethyl)aminoquinazoline
6. 6-Chloro-4-(2-ethoxyethyl)aminoquinazoline
7. 4-(2-n-Propylthioethyl)aminoquinazoline
8. 4-(2-Phenoxyethyl)aminoquinazoline
9. 4-(2-Phenylthioethyl)aminoquinazoline
10. 2-Chloro-4-(2-phenoxyethyl)aminoquinazoline
11. 2-Chloro-4-(2-phenylthioethyl)aminoquinazoline
12. 6-Chloro-4-(2-phenoxyethyl)aminoquinazoline
13. 6-Methyl-4-(2-phenoxyethyl)aminoquinazoline
14. 4-[2-(2-Chlorophenoxy)ethyl]aminoquinazoline
15. 4-[2-(2-Bromophenoxy)ethyl]aminoquinazoline
16. 4-[2-(2-Iodophenoxy)ethyl]aminoquinazoline
17. 4-[2-(2-Fluorophenoxy)ethyl]aminoquinazoline
18. 2-Chloro-4-[2-(2-chlorophenoxy)ethyl]aminoquinazoline
19. 6-Chloro-4-[2-(2-chlorophenoxy)ethyl]aminoquinazoline
20. 4-[2-(2-Methylphenoxy)ethyl]aminoquinazoline
21. 4-[2-(2-Methylphenylthio)ethyl]aminoquinazoline
22. 2-Chloro-4-[2-(2-methylphenoxy)ethyl]aminoquinazoline
23. 6-Chloro-4-[2-(2-methylphenoxy)ethyl]aminoquinazoline
24. 6-Methyl-4-[2-(2-methylphenoxy)ethyl]aminoquinazoline
25. 6-Isopropyl-4-[2-(2-methylphenoxy)ethyl]aminoquinazoline
26. 2-Chloro-4-[2-(2-methylphenylthio)ethyl]aminoquinazoline
27. 4-[2-(2-Ethylphenoxy)ethyl]aminoquinazoline
28. 4-[2-(2-Isopropylphenoxy)ethyl]aminoquinazoline
29. 4-[2-(2-sec-Butylphenoxy)ethyl]aminoquinazoline
30. 4-[2-(2-Methoxyphenoxy)ethyl]aminoquinazoline
31. 6-Methyl-4-[2-(2-methoxyphenoxy)ethyl]aminoquinazoline
32. 4-[2-(2-Ethoxyphenoxy)ethyl]aminoquinazoline
33. 6-Chloro-4-[2-(2-ethoxyphenoxy)ethyl]aminoquinazoline
34. 4-[2-(2-n-Butoxyphenoxy)ethyl]aminoquinazoline
35. 4-[2-(o-Phenylphenoxy)ethyl]aminoquinazoline
36. 4-[2-(p-Phenylphenoxy)ethyl]aminoquinazoline
37. 6-Chloro-4-[2-(o-phenylphenoxy)ethyl]aminoquinazoline
38. 4-[2-(2-Trifluoromethylphenoxy)ethyl]aminoquinazoline
39. 4-[2-(3-Chlorophenoxy)ethyl]aminoquinazoline
40. 6-Methyl-4-[2-(3-chlorophenoxy)ethyl]aminoquinazoline
41. 4-[2-(3-Methylphenoxy)ethyl]aminoquinazoline
42. 4-[2-(3-Methylphenylthio)ethyl]aminoquinazoline
43. 2-Chloro-4-[2-(3-methylphenoxy)ethyl]aminoquinazoline
44. 2-Chloro-4-[2-(3-methylphenylthio)ethyl]aminoquinazoline
45. 4-[2-(3-Trifluoromethylphenoxy)ethyl]aminoquinazoline
46. 4-[2-(4-Chlorophenoxy)ethyl]aminoquinazoline
47. 4-[2-(4-Chlorophenylthio)ethyl]aminoquinazoline
48. 4-[2-(4-Bromophenoxy)ethyl]aminoquinazoline
49. 4-[2-(4-Bromophenylthio)ethyl]aminoquinazoline
50. 4-[2-(4-Fluorophenoxy)ethyl]aminoquinazoline
51. 4-[2-(4-Methylphenoxy)ethyl]aminoquinazoline
52. 4-[2-(4-Methylphenylthio)ethyl]aminoquinazoline
53. 2-Chloro-4-[2-(4-methylphenoxy)ethyl]aminoquinazoline
54. 2-Chloro-4-[2-(4-Methylphenylthio)ethyl]aminoquinazoline
55. 6-Methyl-4-[2-(4-methylphenoxy)ethyl]aminoquinazoline
56. 4-[2-(4-tert-Butylphenoxy)ethyl]aminoquinazoline
57. 4-[2-(4-Methoxyphenoxy)ethyl]aminoquinazoline
58. 4-[2-(4-Isopropoxyphenoxy)ethyl]aminoquinazoline
59. 4-[2-(2,4-Dichlorophenoxy)ethyl]aminoquinazoline
60. 4-[2-(2,4-Dibromophenoxy)ethyl]aminoquinazoline
61. 6-Chloro-4-[2-(2,4-dichlorophenoxy)ethyl]aminoquinazoline
62. 4-[2-(2-Methyl-4-chlorophenoxy)ethyl]aminoquinazoline
63. 2-Chloro-4-[2-(2-methyl-4-chlorophenoxy)ethyl]aminoquinazoline
64. 4-[2-(2,4-Dimethylphenoxy)ethyl]aminoquinazoline
65. 4-[2-(2-Chloro-4-methoxyphenoxy)ethyl]aminoquinazoline
66. 4-[2-(2-Bromo-4-isopropylphenoxy)ethyl]aminoquinazoline
67. 6-Chloro-4-[2-(2,5-dimethylphenoxy)ethyl]aminoquinazoline
68. 4-[2-(2,6-Dimethylphenoxy)ethyl]aminoquinazoline
69. 4-[2-(2,6-Diethylphenoxy)ethyl]aminoquinazoline
70. 2-Chloro-4-[2-(2,6-dimethylphenoxy)ethyl]aminoquinazoline
71. 4-[2-(3-Methyl-4-methylthiophenoxy)ethyl]aminoquinazoline
72. 6-Bromo-[2-(3-methyl-4-n-butylthiophenylthio)ethyl]aminoquinazoline
73. 4-[2-(3,5-Dimethylphenoxy)ethyl]aminoquinazoline
74. 2-Chloro-4-[2-(3,5-dimethylphenoxy)ethyl]aminoquinazoline
75. 6-Chloro-4-[2-(3,5-dimethylphenoxy)ethyl]aminoquinazoline
76. 4-[2-(2,4,5-Trichlorophenoxy)ethyl]aminoquinazoline
77. 4-[2-(2,4,6-Tribromophenoxy)ethyl]aminoquinazoline
78. 6-Chloro-4-[2-(2,4,5-trichlorophenoxy)ethyl]aminoquinazoline
79. 4-[2-(2,4,6-Trichlorophenoxy)ethyl]aminoquinazoline
80. 4-[2-(2,4,6-Triiodophenoxy)ethyl]aminoquinazoline
81. 6-Chloro-4-[2-(2,4,6-trichlorophenoxy)ethyl]aminoquinazoline
82. 4-[2-(2,3,6-Trimethylphenoxy)ethyl]aminoquinazoline 83. 6-Bromo-4-[2-(2,6-dichloro-4-bromophenoxy)ethyl]aminoquinazoline
84. 4-[2-(1-Naphthoxy)ethyl]aminoquinazoline
85. 6-Chloro-4-[2-(1-naphthoxy)ethyl]aminoquinazoline
86. 4-[2-(Benzyloxy)ethyl]aminoquinazoline
87. 4-[2-Benzylthio)ethyl]aminoquinazoline
88. 2-Chloro-4-[2-(benzylthio)ethyl]aminoquinazoline
89. 4-[2-(Phenethyloxy)ethyl]aminoquinazoline
90. 4-[2-(α-Methylbenzyloxy)ethyl]aminoquinazoline
91. 4-(3-Methoxypropyl)aminoquinazoline
92. 4-(3-Ethoxypropyl)aminoquinazoline
93. 2-Chloro-4-(3-ethoxypropyl)aminoquinazoline
94. 6-Nitro-4-(3-ethoxypropyl)aminoquinazoline
95. 4-(3-Isopropoxypropyl)aminoquinazoline
96. 4-(3-n-Butoxypropyl)aminoquinazoline
97. 2-Chloro-4-(3-n-butoxypropyl)aminoquinazoline
98. 4-[3-(2-Ethylhexyloxy)propyl]aminoquinazoline
99. 6-Nitro-4-[3-(2-ethylhexyloxy)propyl]aminoquinazoline
100. 4-(3-Dodecyloxypropyl)aminoquinazoline
101. 6-Iodo-4-(3-stearyloxypropyl)aminoquinazoline
102. 4-(3-Phenoxypropyl)aminoquinazoline
103. 4-(3-Phenylthiopropyl)aminoquinazoline
104. 2-Chloro-4-(3-phenoxypropyl)aminoquinazoline
105. 2-Chloro-4-(3-phenylthiopropyl)aminoquinazoline
106. 6-Methyl-4-(3-phenoxypropyl)aminoquinazoline
107. 6-Methyl-4-(3-phenylthiopropyl)aminoquinazoline
108. 6-Nitro-4-(3-phenoxypropyl)aminoquinazoline
109. 4-[3-(2-Chlorophenoxy)propyl]aminoquinazoline
110. 4-[3-(2-Methylphenoxy)propyl]aminoquinazoline
111. 4-[3-(2-Methylphenylthio)propyl]aminoquinazoline
112. 4-[3-(2-Methoxyphenoxy)propyl]aminoquinazoline
113. 4-[3-(3-Chlorophenoxy)propyl]aminoquinazoline
114. 4-[3-(3-Methylphenoxy)propyl]aminoquinazoline
115. 4-[3-(3-Methylphenylthio)propyl]aminoquinazoline
116. 2-Chloro-4-[3-(3-methylphenoxy)propyl]aminoquinazoline
117. 2-Chloro-4-[3-(3-methylphenylthio)propyl]aminoquinazoline
118. 4-[3-(4-Chlorophenoxy)propyl]aminoquinazoline
119. 2-Chloro-4-[3-(4-chlorophenoxy)propyl]aminoquinazoline
120. 4-[3-(4-Methylphenoxy)propyl]aminoquinazoline
121. 4-[3-(4-Methylphenylthio)propyl]aminoquinazoline
122. 2-Chloro-4-[3-(4-methylphenylthio)propyl]aminoquinazoline
123. 6-Iodo-4-[3-(4-tert-butylphenoxy)propyl]aminoquinazoline
124. 4-[3-(4-methoxyphenoxy)propyl]aminoquinazoline
125. 4-[3-(2,5-Dimethylphenoxy)propyl]aminoquinazoline
126. 4-[3-(2-Methyl-4-chlorophenoxy)propyl]aminoquinazoline
127. 4-[3-(2-Chloro-4-methoxyphenoxy)propyl]aminoquinazoline
128. 4-[3-(3-Methyl-4-chlorophenoxy)propyl]aminoquinazoline
129. 4-[3-(3,5-Dimethylphenoxy)propyl]aminoquinazoline
130. 6-Chloro-4-[3-(2,4,6-trimethylphenoxy)propyl]aminoquinazoline
131. 4-[3-(1-Naphthoxy)propyl]aminoquinazoline
132. 2-Chloro-4-[3-(2-naphthylthio)propyl]aminoquinazoline
133. 4-(1-Methyl-2-methoxyethyl)aminoquinazoline
134. 4-(1-Methyl-2-octyloxyethyl)aminoquinazoline
135. 4-(1-Methyl-2-phenoxyethyl)aminoquinazoline
136. 2-Chloro-4-(1-methyl-2-phenoxyethyl)aminoquinazoline
137. 6-Methyl-4-(1-methyl-2-phenoxyethyl)aminoquinazoline
138. 6-Bromo-4-(1-methyl-2-phenylthioethyl)aminoquinazoline
139. 4-[1-Methyl-2-(2-methylphenoxy)ethyl]aminoquinazoline
140. 4-[1-Methyl-2-(2-methoxyphenoxy)ethyl]aminoquinazoline
141. 4-[1-Methyl-2-(3-chlorophenoxy)ethyl]aminoquinazoline
142. 4-[1-Methyl-2-(3-methylphenoxy)ethyl]aminoquinazoline
143. 4-[1-Methyl-2-(3-isopropylphenylthio)ethyl]aminoquinazoline
144. 4-[1-Methyl-2-(4-chlorophenoxy)ethyl]aminoquinazoline
145. 2-Chloro-4-[1-methyl-2-(4-chlorophenoxy)ethyl]aminoquinazoline
146. 6-Bromo-4-[1-methyl-2-(4-iodophenylthio)ethyl]aminoquinazoline
147. 4-[1-Methyl-2-(4-methylphenoxy)ethyl]aminoquinazoline
148. 2-Chloro-4-[1-methyl-2-(4-methylphenoxy)ethyl]aminoquinazoline
149. 4-[1-Methyl-2-(4-n-butoxyphenoxy)ethyl]aminoquinazoline
150. 4-[1-Methyl-2-(4-phenylphenoxy)ethyl]aminoquinazoline
151. 4-(2-Methyl-2-phenoxyethyl)aminoquinazoline
152. 2-Chloro-4-(2-methyl-2-phenoxyethyl)aminoquinazoline
153. 4-[2-Methyl-2-(2-chlorophenoxy)ethyl]aminoquinazoline
154. 4-[2-Methyl-2-(2-methylphenoxy)ethyl]aminoquinazoline
155. 2-Chloro-4-[2-methyl-2-(2-methylphenoxy)ethyl]aminoquinazoline
156. 6-Chloro-4-[2-methyl-2-(2-tert-butylphenoxy)ethyl]aminoquinazoline
157. 4-[2-Methyl-2-(2-methoxyphenoxy)ethyl]aminoquinazoline
158. 4-[2-Methyl-2-(3-chlorophenoxy)ethyl]aminoquinazoline
159. 4-[2-Methyl-2-(3-methylphenoxy)ethyl]aminoquinazoline
160. 4-[2-Methyl-2-(4-chlorophenoxy)ethyl]aminoquinazoline
161. 4-[2-Methyl-2-(4-bromophenoxy)ethyl]aminoquinazoline
162. 2-Chloro-4-[2-methyl-2-(4-chlorophenoxy)ethyl]aminoquinazoline
163. 4-[2-Methyl-2-(4-methylphenoxy)ethyl]aminoquinazoline
164. 2-Chloro-4-[2-methyl-2-(4-methylphenoxy)ethyl]aminoquinazoline
165. 4-[2-Methyl-2-(4-phenylphenoxy)ethyl]aminoquinazoline
166. 6-Methyl-4-[2-methyl-2-(4-n-butylthiophenoxy)ethyl]aminoquinazoline
167. 4-(4-Ethoxybutyl)aminoquinazoline
168. 4-(4-Dodecylthiobutyl)aminoquinazoline
169. 4-(4-Benzyloxybutyl)aminoquinazoline
170. 4-(4-Phenoxybutyl)aminoquinazoline
171. 6-Methyl-4-(4-phenoxybutyl)aminoquinazoline 172. 4-[4-(2-Chlorophenoxy)butyl]aminoquinazoline
173. 4-[4-(2-Methylphenoxy)butyl]aminoquinazoline
174. 4-[4-(2-Methoxyphenoxy)butyl]aminoquinazoline
175. 4-[4-(3-Methylphenoxy)butyl]aminoquinazoline
176. 4-[4-(3-Chlorophenoxy)butyl]aminoquinazoline
177. 6-Bromo-4-[4-(3-bromophenylthio)butyl]aminoquinazoline
178. 4-[4-(3-Phenylphenoxy)butyl]aminoquinazoline
179. 4-[4-(4-Methylphenoxy)butyl]aminoquinazoline
180. 4-[4-(4-Isopropylphenoxy)butyl]aminoquinazoline
181. 4-[4-(4-Methylthiophenylthio)butyl]aminoquinazoline
182. 4-(2-Ethyl-2-benzyloxyethyl)aminoquinazoline
183. 4-(2-Ethyl-2-phenoxyethyl)aminoquinazoline
184. 4-[2-Ethyl-2-(2-methoxyphenoxy)ethyl]aminoquinazoline
185. 2-Chloro-4-[2-ethyl-2-(4-chlorophenoxy)ethyl]aminoquinazoline
186. 4-(1-Ethyl-2-methoxyethyl)aminoquinazoline
187. 6-Bromo-4-(1-ethyl-2-benzyloxyethyl)aminoquinazoline
188. 2-Chloro-4-(1-ethyl-2-phenoxyethyl)aminoquinazoline
189. 4-[1-Ethyl-2-(2-chlorophenoxy)ethyl]aminoquinazoline
190. 4-[1-Ethyl-2-(3-methylphenoxy)ethyl]aminoquinazoline
191. 4-[1-Ethyl-2-(4-isopropoxyphenylthio)ethyl]aminoquinazoline
192. 4-(2,2-Dimethyl-2-ethoxyethyl)aminoquinazoline
193. 2-Chloro-4-(2,2-dimethyl-2-octyloxyethyl)aminoquinazoline
194. 6-Methyl-4-(2,2-dimethyl-2-benzylthioethyl)aminoquinazoline
195. 4-(2,2-Dimethyl-2-phenoxyethyl)aminoquinazoline
196. 2-Chloro-4-(2,2-dimethyl-2-phenoxyethyl)aminoquinazoline
197. 4-[2,2-Dimethyl-2-(chlorophenoxy)ethyl]aminoquinazoline
198. 4-[2,2-Dimethyl-2-(2-methylphenoxy)ethyl]aminoquinazoline
199. 2-Chloro-4-[2,2-dimethyl-2-(2-methylphenoxy)ethyl]aminoquinazoline
200. 4-[2,2-Dimethyl-2-(2-methoxyphenoxy)ethyl]aminoquinazoline
201. 4-[2,2-Dimethyl-2-(3-chlorophenoxy)ethyl]aminoquinazoline
202. 4-[2,2-Dimethyl-2-(3-methylphenoxy)ethyl]aminoquinazoline
203. 2-Chloro-4-[2,2-dimethyl-2-(3-methylphenoxy)ethyl]aminoquinazoline
204. 4-[2,2-Dimethyl-2-(4-chlorophenoxy)ethyl]aminoquinazoline
205. 4-[2,2-Dimethyl-2-(4-bromophenoxy)ethyl]aminoquinazoline
206. 4-[2,2-Dimethyl-2-(4-methylphenoxy)ethyl]aminoquinazoline
207. 4-[2,2-Dimethyl-2-(4-isopropylphenylthio)ethyl]aminoquinazoline
208. 2-Chloro-4-[2,2-dimethyl-2-(4-methylphenoxy)ethyl]aminoquinazoline
209. 4-(1,1-Dimethyl-2-phenoxyethyl)aminoquinazoline
210. 4-[1,1-Dimethyl-2-(2-methylphenoxy)ethyl]aminoquinazoline
211. 4-[1,1-Dimethyl-2-(3-methoxyphenoxy)ethyl]aminoquinazoline
212. 4-(1,2-Dimethyl-2-dodecyloxyethyl)aminoquinazoline
213. 4-(1,2-Dimethyl-2-phenoxyethyl)aminoquinazoline
214. 4-[1,2-Dimethyl-2-(2-chlorophenoxy)ethyl]aminoquinazoline
215. 4-[1,2-Dimethyl-2-(3-methylphenoxy)ethyl]aminoquinazoline
216. 2-Chloro-4-[1,2-dimethyl-2-(4-methoxyphenylthio)ethyl]aminoquinazoline
217. 4-(5-n-Butoxypentyl)aminoquinazoline
218. 4-(5-Octoxypentyl)aminoquinazoline
219. 4-[5-(2-Ethylhexyloxy)pentyl]aminoquinazoline
220. 4-(5-Stearyloxypentyl)aminoquinazoline
221. 4-(5-Benzylthiopentyl)aminoquinazoline
222. 4-(5-Phenoxypentyl)aminoquinazoline
223. 4-[5-(2-Chlorophenoxy)pentyl]aminoquinazoline
224. 2-Chloro-4-[5-(2-chlorophenoxy)pentyl]aminoquinazoline
225. 4-[5-(2-Methylphenoxy)pentyl]aminoquinazoline
226. 4-[5-(2-Methoxyphenoxy)pentyl]aminoquinazoline
227. 2-Chloro-4-[5-(2-methoxyphenylthio)pentyl]aminoquinazoline
228. 4-[5-(3-Chlorophenoxy)pentyl]aminoquinazoline
229. 4-[5-(3-Methylphenoxy)pentyl]aminoquinazoline
230. 4-[5-(3-Methoxyphenoxy)pentyl]aminoquinazoline
231. 4-[5-(4-Chlorophenoxy)pentyl]aminoquinazoline
232. 4-[5-(4-Methylphenoxy)pentyl]aminoquinazoline
233. 4-[5-(4-Methoxyphenoxy)pentyl]aminoquinazoline
234. 4-(6-Phenoxyhexyl)aminoquinazoline
235. 4-[6-(2-Chlorophenoxy)hexyl]aminoquinazoline
236. 4-[6-(2-Methylphenoxy)hexyl]aminoquinazoline
237. 6-Chloro-4-[6-(2-methylphenoxy)hexyl]aminoquinazoline
238. 4-[6-(3-Chlorophenoxy)hexyl]aminoquinazoline
239. 4-[6-(3-Methylphenoxy)hexyl]aminoquinazoline
240. 4-[6-(3-Methoxyphenoxy)hexyl]aminoquinazoline
241. 4-[6-(4-Chlorophenoxy)hexyl]aminoquinazoline
242. 4-[6-(4-Chlorophenylthio)hexyl]aminoquinazoline
243. 4-[6-(4-Methylphenoxy)hexyl]aminoquinazoline
244. 4-[6-(4-Methoxyphenoxy)hexyl]aminoquinazoline
245. 2-Chloro-4-[6-(4-methoxyphenoxy)hexyl]aminoquinazoline
246. 4-(7-Isopropoxyheptyl)aminoquinazoline
247. 4-(7-Dodecylthioheptyl)aminoquinazoline
248. 4-(7-Phenoxyheptyl)aminoquinazoline
249. 4-[7-(2-Chlorophenoxy)heptyl]aminoquinazoline
250. 4-[7-(2-Methylphenoxy)heptyl]aminoquinazoline
251. 4-[7-(2-Methoxyphenoxy)heptyl]aminoquinazoline
252. 4-[7-(3-Chlorophenoxy)heptyl]aminoquinazoline
253. 4-[7-(3-Methylphenoxy)heptyl]aminoquinazoline
254. 4-[7-(4-Chlorophenoxy)heptyl]aminoquinazoline
255. 4-[7-(4-Methylphenoxy)heptyl]aminoquinazoline
256. 4-[7-(4-Methoxyphenoxy)heptyl]aminoquinazoline
257. 4-[7-(2,4-Dichlorophenoxy)heptyl]aminoquinazoline
258. 4-[7-(3,5-Dimethylphenoxy)heptyl]aminoquinazoline
259. 4-(8-Methoxyoctyl)aminoquinazoline
260. 4-(8-Benzylthiooctyl)aminoquinazoline
261. 4-(8-Phenoxyoctyl)aminoquinazoline
262. 4-[8-(2-Chlorophenoxy)octyl]aminoquinazoline
263. 4-[8-(2-Methylphenoxy)octyl]aminoquinazoline
264. 4-[8-(2-Methoxyphenoxy)octyl]aminoquinazoline
265. 4-[8-(3-Chlorophenoxy)octyl]aminoquinazoline
266. 4-[8-(3-Methylphenyl)octyl]aminoquinazoline
267. 4-[8-(3-Methoxyphenyl)octyl]aminoquinazoline
268. 4-[8-(4-Chlorophenoxy)octyl]aminoquinazoline
269. 4-[8-(4-Methylphenoxy)octyl]aminoquinazoline
270. 4-[8-(4-Methylthiophenoxy)octyl]aminoquinazoline 271. 4-[8-(4-Methoxyphenoxy)octyl]aminoquinazoline
272. 4-[8-(3,5-Dichlorophenoxy)octyl]aminoquinazoline
273. 4-[8-(2,6-Dimethylphenoxy)octyl]aminoquinazoline
274. 4-(10-Methoxydecyl)aminoquinazoline
275. 4-(10-Phenoxydecyl)aminoquinazoline
276. 4-[10-(2-Chlorophenoxy)decyl]aminoquinazoline
277. 4-[10-(3-Methylphenoxy)decyl]aminoquinazoline
278. 4-[10-(4-Methoxyphenoxy)decyl]aminoquinazoline
279. 4-(12-Phenoxydodecyl)aminoquinazoline
280. 4-[12-(2-Methylphenoxy)dodecyl]aminoquinazoline
281. 4-[12-(3-Chlorophenoxy)dodecyl]aminoquinazoline
282. 4-[12-(4-Methoxyphenoxy)dodecyl]aminoquinazoline
283. 4-(16-Phenoxyhexadecyl)aminoquinazoline
284. 4-(18-Phenoxyoctadecyl)aminoquinazoline
285. 4-[2-(2-n-Propylphenoxy)ethyl]aminoquinazoline
286. 6-Methyl-4-[4-(2-chlorophenoxy)butyl]aminoquinazoline
287. 4-[2-(2-Methoxy-4-methylphenoxy)ethyl]aminoquinazoline
288. 4-[2-(3-Methoxyphenoxy)ethyl]aminoquinazoline
289. 4-[2-(2-Methoxy-4-chlorophenoxy)ethyl]aminoquinazoline
290. 4-[2-(2-Methyl-3-chlorophenoxy)ethyl]aminoquinazoline
291. 2-Methyl-4-(3-phenoxypropyl)aminoquinazoline
292. 4-[2-(2,5-Dimethoxyphenoxy)ethyl]aminoquinazoline
293. 4-[2-(3,5-Dimethyl-4-bromophenoxy)ethyl]aminoquinazoline
294. 4-[2-(2,4-Dichloro-6-methylphenoxy)ethyl]aminoquinazoline
295. 4-[2-(2-Trifluoromethyl-4-chlorophenoxy)ethyl]aminoquinazoline
296. 4-[2-(2-n-Butylphenoxy)ethyl]aminoquinazoline
297. 4-[2-(2-tert-Butylphenoxy)ethyl]aminoquinazoline The compounds of formula (I) may readily be prepared, for example, by the following methods which can be performed under per se known conditions:

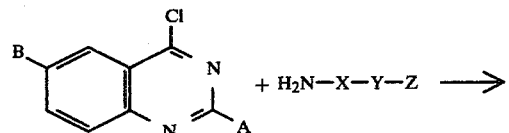  (1)

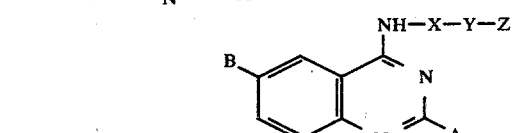  (2)

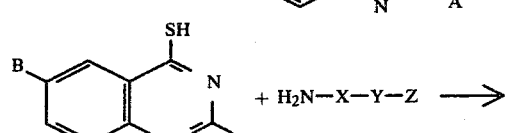  (3)

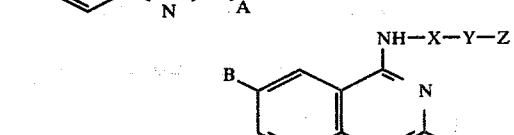

(In the above formulae, A, B, X, Y and Z are as defined above).

The reaction is preferably carried out in the presence of a solvent and a base.

The nature of the solvent is not critical, provided that it has no adverse effect upon the reaction. Examples of suitable solvents include: Chlorinated or non-chlorinated aromatic, aliphatic or alicyclic hydrocarbons, such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers, such as diethyl ether, ethylene glycol dimethyl ether, tetrahydrofuran and dioxane; ketones, such as acetone and methyl ethyl ketone; alcohols, such as methanol, ethanol and ethylene glycol as well as mixtures thereof with water; and mixtures of the above-mentioned solvents.

Examples of bases include: organic bases, such as triethylamine, pyridine and N,N-diethylaniline; inorganic bases such as sodium hydroxide, potassium hydroxide, sodium carbonate and potassium carbonate.

The reaction temperature is not critical and it ranges usually from ambient to a temperature at which the solvent used refluxes. It is preferable that the reaction is performed with heating in order to shorten the reaction period.

After completion of the reaction, the desired compound may optionally be purified by conventional methods such as recrystallization or chromatography.

Acid addition salts may readily be prepared by introducing an acid into the reaction mixture and then by evaporating the solvent.

Similarly, hydrates may usually be obtained by recrystallizing the desired compound from a solvent containing water.

Preparation of the active ingredient compound of the invention is illustrated by the following Examples:

Preparation 1. Compound No. 19

To a solution of 2.0 g (0.01 mol) of 4,6-dichloroquinazoline in 50 ml of benzene were added 1.0 g (0.01 mol) of triethylamine and 1.7 g (0.01 mol) of 2-(2-chlorophenoxy) ethylamine, and the mixture was refluxed, with stirring, for 3 hours.

After completion of the reaction, the benzene was removed from the reaction mixture by evaporation under reduced pressure, and the crystals which were separated were washed with water and collected by filtration. Recrystallization of the crystals from ethanol gave 2.7 g of 6-chloro-4-[2-(2-chlorophenoxy)ethyl]aminoquinazoline in the form of colorless plates.
m.p. 176°~178° C.
Elementary analysis (%): Calcd: C, 57.62; H, 3.78; N, 12.69. Found: C, 57.50; H, 3.92; N, 12.57.

Preparation 2. Compound No. 31

To a solution of 1.8 g (0.01 mol) of 4-chloro-6-methyl-quinazoline in 50 ml of benzene were added 1.0 g (0.01 mol) of triethylamine and 1.7 g (0.01 mol) of 2-(O-methoxyphenoxy)ethylamine, and the mixture was heated, with stirring, at 60°~70° C. for 5 hours. After completion of the reaction, the benzene was evaporated under reduced pressure and the residue was dissolved in chloroform, washed with water and dried over anhydrous sodium sulfate. The chloroform was evaporated under reduced pressure to leave crystals, which were recrystallized from ethanol, giving 0.9 g of 6-methyl-4-[2-(2-methoxyphenoxy)ethyl]-aminoquinazoline in the form of colorless plates.

m.p. 167°~169° C.

Elementary analysis (%): Calcd: C, 69.88; H, 6.19; N, 13.58 Found: C, 69.86; H, 6.15; N, 13.60

Preparation 3. Compound No. 49

To a solution of 2.5 g (0.015 mol) of 4-chloroquinazoline in 50 ml of benzene were added 1.5 g (0.015 mol) of triethylamine and 3.5 g (0.015 mol) of 2-(p-bromophenylthio) ethylamine, and the mixture was heated, with stirring, at 70°~80° C. for 3 hours. After completion of the reaction, the benzene was evaporated under reduced pressure and the resulting crystals were washed with water, collected by filtration and recrystallized from ethanol, giving 3.0 g of 4-[2-(4-bromophenylthio)ethyl]aminoquinazoline in the form of colorless granules.

m.p. 161°~163° C.

Elementary analysis (%): Calcd: C, 52.95; H, 3.85; N, 11.41. Found: C, 53.34; H, 3.92; N, 11.66.

Preparation 4. Compound No. 86

To a solution of 3.3 g (0.02 mol) of 4-chloroquinazoline in 50 ml of benzene were added 2.0 g (0.02 mol) of triethylamine and 3.0 g (0.02 mol) of 2-benzyloxyethylamine, and the mixture was heated, with stirring, at 60°~70° C. for 5 hours. After completion of the reaction, the benzene was evaporated under reduced pressure, and the resulting crystals were washed with water, collected by filtration, dried and recrystallized from benzene/n-hexane, affording 3.7 g of 4-[2-(benzyloxy)ethyl]aminoquinazoline in the form of colorless needles.

m.p. 111°~113° C.

Elementary analysis (%): Calcd: C, 73.09; H, 6.14; N, 15.04. Found: C, 72.98; H, 6.11; N, 14.69.

Preparation 5. Compound No. 102

To a solution of 2.5 g (0.015 mol) of 4-chloroquinazoline in 50 ml of benzene were added 1.5 g (0.015 mol) of triethylamine and 2.3 g (0.015 mol) of 3-phenoxy-propylamine, and the mixture was refluxed for 3 hours. After completion of the reaction, the benzene was evaporated under reduced pressure and the residue was washed with water, collected by filtration to give crystals. The crystals were recrystallized from 70% ethanol, giving 1.5 g of 4-(3-phenoxypropyl)aminoquinazoline in the form of colorless flakes.

m.p. 129°~131° C.

Elementary analysis (%): Calcd: C, 73.09; H. 6.14; N, 15.04. Found: C, 72.69; H, 6.24; N, 14.66.

Preparation 6. Compound No. 108

To a solution of 1.7 g (0.008 mol) of 4-chloro-5-nitroquinazoline in 50 ml of benzene were added 0.8 g (0.008 mol) of triethylamine and 1.2 g (0.008 mol) of 3-phenoxypropylamine, and the mixture was refluxed for 3 hours on an oil bath. After cooling, crystals separated were collected by filtration, washed with water and recrystallized from aqueous ethanol, affording 6-nitro-4-(3-phenoxypropyl)aminoquinazoline as the monohydrate in the form of yellow needles.

m.p. 121°~123° C.

Elementary analysis (%): Calcd: C, 60.38; H, 5.19; N, 16.44. Found: C, 59.65; H, 5.26; N, 16.37.

Preparation 7. Compound No. 208

To a solution of 2.0 g (0.01 mol) of 2,4-dichloroquinazoline in 50 ml of benzene were added 1.0 g (0.01 mol) of triethylamine and 1.8 g (0.01 mol) of 2,2-dimethyl-2-(4-methylphenoxy)-ethylamine and the mixture was stirred at an ambient temperature for 4 hours. After completion of the reaction, the benzene was evaporated under reduced pressure, and the residue was dissolved in chloroform, washed with water and dried over anhydrous sodium sulfate. The chloroform was removed by evaporation under reduced pressure to leave crystals, which were recrystallized from benzene/hexane, affording 2.3 g of 2-chloro-4-[2,2-dimethyl-2-(4-methylphenoxy)ethyl]-aminoquinazoline in the form of a colorless fine powder.

m.p. 121°~124° C.

Elementary analysis (%): Calcd: C, 66.76; H, 5.90; N, 12.29. Found: C, 66.52; H, 6.04; N, 11.93.

Preparation 8. Compound No. 222

To a solution of 1.7 g (0.01 mol) of 4-chloroquinazoline in 50 ml of benzene were added 1.0 g (0.01 mol) of triethylamine and 1.8 g (0.01 mol) of 5-phenoxypentylamine, and the mixture was refluxed for 3 hours. After completion of the reaction, the benzene was evaporated under reduced pressure to leave crystals, which were washed with water, collected by filtration and recrystallized from aqueous ethanol, giving 0.6 g of 4-(5-phenoxypentyl)aminoquinazoline in the form of colorless flakes.

m.p. 106°~108° C.

Elementary analysis (%): Calcd: C, 74.26; H, 6.84; N, 13.68. Found: C, 74.95; H, 6.89; N, 13.75.

2.5 g of the 4-(5-phenoxypentyl)aminoquinazoline obtained according to the process were dissolved in 100 ml of ethanol, and 2 g of 36% hydrochloric acid were added. The ethanol was removed by evaporation under reduced pressure and the resulting residue was dried, recrystallized from aqueous ethanol, giving 4-(5-phenoxypentyl)aminoquinazoline in the form of the hydrochloride melting at 183°~186° C.

Following the methods described in Preparations 1 to 8, the following compounds were obtained:

4-(2-Methoxyethyl)aminoquinazoline
m.p. 127°~128° C.

4-(2-Ethoxyethyl)aminoquinazoline
m.p. 112°~113° C.

4-(2-Ethylthioethyl)aminoquinazoline
m.p. 116°~118° C.

2-Chloro-4-(2-ethoxyethyl)aminoquinazoline
m.p. 93°~95° C.

2-Chloro-4-(2-ethylthioethyl)aminoquinazoline
m.p. 119°~121° C.

6-Chloro-4-(2-ethoxyethyl)aminoquinazoline
m.p. 125°~127° C.

4-(2-n-Propylthioethyl)aminoquinazoline
m.p. 95°~98° C.

4-(2-Phenoxyethyl)aminoquinazoline
 m.p. 183°~185° C.
4-(2-Phenylthioethyl)aminoquinazoline
 m.p. 137°~139° C.
2-Chloro-4-(2-phenoxyethyl)aminoquinazoline
 m.p. 172°~174° C.
2-Chloro-4-(2-phenylthioethyl)aminoquinazoline
 m.p. 210°~212° C.
6-Chloro-4-(2-phenoxyethyl)aminoquinazoline
 m.p. 155°~158° C.
6-Methyl-4-(2-phenoxyethyl)aminoquinazoline
 m.p. 138°~140° C.
4-[2-(2-Chlorophenoxy)ethyl]aminoquinazoline
 m.p. 161°~163° C.
4-[2-(2-Bromophenoxy)ethyl]aminoquinazoline
 m.p. 164°~166° C.
4-[2-(2-Iodophenoxy)ethyl]aminoquinazoline
 m.p. 161°~163° C.
4-[2-(2-Fluorophenoxy)ethyl]aminoquinazoline
 m.p. 164°~166° C.
2-Chloro-4-[2-(2-chlorophenoxy)ethyl]aminoquinazoline
 m.p. 169°~171° C.
4-[2-(2-Methoxyphenoxy)ethyl]aminoquinazoline
 m.p. 138°~140° C.
4-[2-(2-Methylphenylthio)ethyl]aminoquinazoline
 m.p. 149°~151° C.
2-Chloro-4-[2-(2-methylphenoxy)ethyl]aminoquinazoline
 m.p. 176°~178° C.
6-Chloro-4-[2-(2-methylphenoxy)ethyl]aminoquinazoline
 m.p. 168°~171° C.
6-Methyl-4-[2-(2-methylphenoxy)ethyl]aminoquinazoline
 m.p. 161°~164° C.
2-Chloro-4-[2-(2-methylphenylthio)ethyl]aminoquinazoline
 m.p. 194°~196° C.
4-[2-(2-Ethylphenoxy)ethyl]aminoquinazoline
 m.p. 134°~135° C.
4-[2-(2-Isopropylphenoxy)ethyl]aminoquinazoline
 m.p. 132°~134° C.
4-[2-(2-sec-Butylphenoxy)ethyl]aminoquinazoline
 m.p. 128°~130° C.
4-[2-(2-Methoxyphenoxy)ethyl]aminoquinazoline
 m.p. 148°~152° C.
4-[2-(2-Ethoxyphenoxy)ethyl]aminoquinazoline.monohydrate
 m.p. 111°~113° C.
6-Chloro-4-[2-(2-ethoxyphenoxy)ethyl]aminoquinazoline.monohydrate
 m.p. 154°~156° C.
4-[2-(2-Phenylphenoxy)ethyl]aminoquinazoline
 m.p. 137°~140° C.
4-[2-(3-Chlorophenoxy)ethyl]aminoquinazoline
 m.p. 193°~195° C.
6-Methyl-4-[2-(3-chlorophenoxy)ethyl]aminoquinazoline
 m.p. 150°~152° C.
4-[2-(3-Methylphenoxy)ethyl]aminoquinazoline
 m.p. 184°~186° C.
4-[2-(3-Methylphenylthio)ethyl]aminoquinazoline
 m.p. 131°~133° C.
2-Chloro-4-[2-(3-methylphenoxy)ethyl]aminoquinazoline
 m.p. 162°~164° C.
2-Chloro-4-[2-(3-methylphenylthio)ethyl]aminoquinazoline
 m.p. 154°~156° C.
4-[2-(3-Trifluoromethylphenoxy)ethyl]aminoquinazoline
 m.p. 161°~163° C.
4-[2-(4-Chlorophenoxy)ethyl]aminoquinazoline
 m.p. 191°~193° C.
4-[2-(4-Chlorophenylthio)ethyl]aminoquinazoline
 m.p. 147°~149° C.
4-[2-(4-Bromophenoxy)ethyl]aminoquinazoline
 m.p. 161°~163° C.
4-[2-(4-Fluorophenoxy)ethyl]aminoquinazoline
 m.p. 189°~190° C.
4-[2-(4-Methylphenoxy)ethyl]aminoquinazoline
 m.p. 153°~155° C.
4-[2-(4-Methylphenylthio)ethyl]aminoquinazoline
 m.p. 134°~136° C.
2-Chloro-4-[2-(4-methylphenoxy)ethyl]aminoquinazoline
 m.p. 161°~163° C.
2-Chloro-4-[2-(4-methylphenylthio)ethyl]aminoquinazoline
 m.p. 160°~165° C.
6-Methyl-4-[2-(4-methylphenoxy)ethyl]aminoquinazoline
 m.p. 143°~145° C.
4-[2-(4-tert-Butylphenoxy)ethyl]aminoquinazoline
 m.p. 138°~143° C.
4-[2-(4-Methoxyphenoxy)ethyl]aminoquinazoline
 m.p. 142°~144° C.
4-[2-(2,4-Dichlorophenoxy)ethyl]aminoquinazoline
 m.p. 170°~172° C.
4-[2-(2,4-Dibromophenoxy)ethyl]aminoquinazoline
 m.p. 161°~163° C.
6-Chloro-4-[2-(2,4-dichlorophenoxy)ethyl]aminoquinazoline
 m.p. 187°~188° C.
4-[2-(2-Methyl-4-chlorophenoxy)ethyl]aminoquinazoline
 m.p. 164°~166° C.
2-Chloro-4-[2-(2-methyl-4-chlorophenoxy)ethyl]aminoquinazoline
 m.p. 179°~181° C.
4-[2-(2,4-Dimethylphenoxy)ethyl]aminoquinazoline
 m.p. 164°~167° C.
4-[2-(2-Chloro-4-methoxyphenoxy)ethyl]aminoquinazoline
 m.p. 124°~126° C.
6-Chloro-4-[2-(2,5-dimethylphenoxy)ethyl]aminoquinazoline
 m.p. 164°~167° C.
4-[2-(2,6-Dimethylphenoxy)ethyl]aminoquinazoline
 m.p. 132°~134° C.
2-Chloro-4-[2-(2,6-dimethylphenoxy)ethyl]aminoquinazoline
 m.p. 169°~171° C.
4-[2-(3-Methyl-4-methylthiophenoxy)ethyl]aminoquinazoline
 m.p. 171°~173° C.
4-[2-(3,5-Dimethylphenoxy)ethyl]aminoquinazoline
 m.p. 183°~185° C.
2-Chloro-4-[2-(3,5-dimethylphenoxy)ethyl]aminoquinazoline
 m.p. 186°~188° C.
6-Chloro-4-[2-(3,5-dimethylphenoxy)ethyl]aminoquinazoline
 m.p. 209°~211° C.

4-[2-(2,4,5-Trichlorophenoxy)ethyl]aminoquinazoline
  m.p. 176°~178° C.
6-Chloro-4-[2-(2,4,5-trichlorophenoxy)ethyl]aminoquinazoline
  m.p. 198°~202° C.
4-[2-(2,4,6-Trichlorophenoxy)ethyl]aminoquinazoline
  m.p. 170°~172° C.
4-[2-(2,4,6-Triiodophenoxy)ethyl]aminoquinazoline
  m.p. 185°~187° C.
4-[2-(2,4,6-Tribromophenoxy)ethyl]aminoquinazoline
  m.p. 181°~183° C.
4-[2-(1-Naphthoxy)ethyl]aminoquinazoline
  m.p. 163°~165° C.
6-Chloro-4-[2-(1-naphthoxy)ethyl]aminoquinazoline
  m.p. 165°~167° C.
4-[2-Benzylthio)ethyl]aminoquinazoline
  m.p. 111°~113° C.
2-Chloro-4-[2-(benzylthio)ethyl]aminoquinazoline
  m.p. 107°~109° C.
4-(3-Methoxypropyl)aminoquinazoline
  m.p. 105°~107° C.
4-(3-Ethoxypropyl)aminoquinazoline
  m.p. 101°~103° C.
2-Chloro-4-(3-ethoxypropyl)aminoquinazoline
  m.p. 92°~95° C.
6-Nitro-4-(3-ethoxypropyl)aminoquinazoline
  m.p. 141°~143° C.
4-(3-Isopropoxypropyl)aminoquinazoline
  m.p. 84°~86° C.
4-(3-n-Butoxypropyl)aminoquinazoline
  m.p. 77°~79° C.
2-Chloro-4-(3-n-butoxypropyl)aminoquinazoline
  m.p. 86°~88° C.
4-[3-(2-Ethylhexyloxy)propyl]aminoquinazoline
  m.p. 36°~40° C.
6-Nitro-4-[3-(2-ethylhexyloxy)propyl]aminoquinazoline
  m.p. 55°~58° C.
4-(3-Phenylthiopropyl)aminoquinazoline
  m.p. 103°~105° C.
2-Chloro-4-(3-phenoxypropyl)aminoquinazoline
  m.p. 118°~120° C.
2-Chloro-4-(3-phenylthiopropyl)aminoquinazoline
  m.p. 86°~89° C.
6-Methyl-4-(3-phenoxypropyl)aminoquinazoline
  m.p. 121°~123° C.
6-Methyl-4-(3-phenylthiopropyl)aminoquinazoline
  m.p. 121°~123° C.
4-[3-(2-Chlorophenoxy)propyl]aminoquinazoline
  m.p. 144°~145° C.
4-[3-(2-Methylphenoxy)propyl]aminoquinazoline
  m.p. 147°~149° C.
4-[3-(2-Methylphenylthio)propyl]aminoquinazoline
  m.p. 99°~102° C.
4-[3-(2-Methoxyphenoxy)propyl]aminoquinazoline
  m.p. 138°~139° C.
4-[3-(3-Chlorophenoxy)propyl]aminoquinazoline
  m.p. 145°~147° C.
4-[3-(3-Methylphenoxy)propyl]aminoquinazoline
  m.p. 153°~155° C.
4-[3-(3-Methylphenylthio)propyl]aminoquinazoline
  m.p. 73°~76° C.
2-Chloro-4-[3-(3-methylphenoxy)propyl]aminoquinazoline
  m.p. 96°~99° C.
2-Chloro-4-[3-(3-methylphenylthio)propyl]aminoquinazoline
  m.p. 70°~73° C.
4-[3-(4-Chlorophenoxy)propyl]aminoquinazoline
  m.p. 148°~150° C.
2-Chloro-4-[3-(4-chlorophenoxy)propyl]aminoquinazoline
  m.p. 131°~133° C.
4-[3-(4-Methylphenoxy)propyl]aminoquinazoline
  m.p. 151°~152° C.
4-[3-(4-Methylphenylthio)propyl]aminoquinazoline
  m.p. 129°~131° C.
2-Chloro-4-[3-(4-methylphenylthio)propyl]aminoquinazoline
  m.p. 82°~85° C.
4-[3-(4-Methoxyphenoxy)propyl]aminoquinazoline
  m.p. 136°~138° C.
4-[3-(2,5-Dimethylphenoxy)propyl]aminoquinazoline
  m.p. 142°~144° C.
4-[3-(2-Methyl-4-chlorophenoxy)propyl]aminoquinazoline
  m.p. 178°~181° C.
4-[3-(2-Chloro-4-methoxyphenoxy)propyl]aminoquinazoline
  m.p. 166°~169° C.
4-[3-(3-Methyl-4-chlorophenoxy)propyl]aminoquinazoline
  m.p. 137°~139° C.
4-[3-(3,5-Dimethylphenoxy)propyl]aminoquinazoline
  m.p. 116°~118° C.
4-[3-(1-Naphthoxy)propyl]aminoquinazoline
  m.p. 132°~134° C.
4-(1-Methyl-2-phenoxyethyl)aminoquinazoline
  m.p. 125°~128° C.
2-Chloro-4-(1-methyl-2-phenoxyethyl)aminoquinazoline
  m.p. 168°~170° C.
6-Methyl-4-(1-methyl-2-phenoxyethyl)aminoquinazoline
  m.p. 150°~152° C.
4-[1-Methyl-2-(2-methylphenoxy)ethyl]aminoquinazoline
  m.p. 134°~136° C.
4-[1-Methyl-2-(2-methoxyphenoxy)ethyl]aminoquinazoline
  m.p. 165°~167° C.
4-[1-Methyl-2-(3-chlorophenoxy)ethyl]aminoquinazoline
  m.p. 163°~166° C.
4-[1-Methyl-2-(3-methylphenoxy)ethyl]aminoquinazoline
  m.p. 130°~132° C.
4-[1-Methyl-2-(4-chlorophenoxy)ethyl]aminoquinazoline
  m.p. 156°~159° C.
2-Chloro-4-[1-methyl-2-(4-chlorophenoxy)ethyl]aminoquinazoline
  m.p. 125°~128° C.
4-[1-Methyl-2-(4-methylphenoxy)ethyl]aminoquinazoline
  m.p. 171°~173° C.
2-Chloro-4-[1-methyl-2-(4-methylphenoxy)ethyl]aminoquinazoline
  m.p. 139°~141° C.
4-(2-Methyl-2-phenoxyethyl)aminoquinazoline
  m.p. 162°~164° C.
2-Chloro-4-(2-methyl-2-phenoxyethyl)aminoquinazoline
  m.p. 144°~146° C.
4-[2-Methyl-2-(2-chlorophenoxy)ethyl]aminoquinazoline
  m.p. 151°~153° C.

4-[2-Methyl-2-(2-methylphenoxy)ethyl]aminoquinazoline
m.p. 152°~154° C.

2-Chloro-4-[2-methyl-2-(2-methylphenoxy)ethyl]aminoquinazoline
m.p. 122°~125° C.

4-[2-Methyl-2-(2-methoxyphenoxy)ethyl]aminoquinazoline
m.p. 135°~138° C.

4-[2-Methyl-2-(3-chlorophenoxy)ethyl]aminoquinazoline
m.p. 140°~142° C.

4-[2-Methyl-2-(3-methylphenoxy)ethyl]aminoquinazoline
m.p. 123°~126° C.

4-[2-Methyl-2-(4-chlorophenoxy)ethyl]aminoquinazoline
m.p. 165°~168° C.

2-Chloro-4-[2-methyl-2-(4-chlorophenoxy)ethyl]aminoquinazoline
m.p. 160°~162° C.

4-[2-Methyl-2-(4-methylphenoxy)ethyl]aminoquinazoline
m.p. 163°~164° C.

2-Chloro-4-[2-methyl-2-(4-methylphenoxy)ethyl]aminoquinazoline
m.p. 138°~141° C.

4-(4-Phenoxybutyl)aminoquinazoline.monohydrate
m.p. 90°~93° C.

6-Methyl-4-(4-phenoxybutyl)aminoquinazoline
m.p. 110°~112° C.

4-[4-(2-Chlorophenoxy)butyl]aminoquinazoline
m.p. 151°~153° C.

4-[4-(2-Methylphenoxy)butyl]aminoquinazoline
m.p. 152°~153° C.

4-[4-(2-Methoxyphenoxy)butyl]aminoquinazoline
m.p. 135°~137° C.

4-[4-(3-Methylphenoxy)butyl]aminoquinazoline
m.p. 110°~112° C.

4-[4-(4-Methylphenoxy)butyl]aminoquinazoline
m.p. 121°~123° C.

4-(2-Ethyl-2-phenoxyethyl)aminoquinazoline
m.p. 158°~160° C.

4-(2,2-Dimethyl-2-phenoxyethyl)aminoquinazoline
m.p. 98°~100° C.

2-Chloro-4-(2,2-dimethyl-2-phenoxyethyl)aminoquinazoline
m.p. 132°~134° C.

4-[2,2-Dimethyl-2-(2-chlorophenoxy)ethyl]aminoquinazoline
m.p. 89°~91° C.

4-[2,2-Dimethyl-2-(2-methylphenoxy)ethyl]aminoquinazoline
m.p. 96°~99° C.

2-Chloro-4-[2,2-dimethyl-2-(2-methylphenoxy)ethyl]aminoquinazoline
m.p. 110°~112° C.

4-[2,2-Dimethyl-2-(2-methoxyphenoxy)ethyl]aminoquinazoline
m.p. 103~105° C.

4-[2,2-Dimethyl-2-(3-chlorophenoxy)ethyl]aminoquinazoline
m.p. 111°~113° C.

4-[2,2-Dimethyl-2-(3-methylphenoxy)ethyl]aminoquinazoline
m.p. 97°~100° C.

2-Chloro-4-[2,2-dimethyl-2-(3-methylphenoxy)ethyl]aminoquinazoline
m.p. 103°~106° C.

4-[2,2-Dimethyl-2-(4-chlorophenoxy)ethyl]aminoquinazoline
m.p. 104°~106° C.

4-[2,2-Dimethyl-2-(4-methylphenoxy)ethyl]aminoquinazoline
m.p. 92°~94° C.

4-[5-(2-Chlorophenoxy)pentyl]aminoquinazoline
m.p. 115°~117° C.

4-[5-(2-Methylphenoxy)pentyl]aminoquinazoline
m.p. 96°~98° C.

4-[5-(2-Methoxyphenoxy)pentyl]aminoquinazoline
m.p. 104°~106° C.

4-[5-(3-Methylphenoxy)pentyl]aminoquinazoline
m.p. 113°~115° C.

4-[5-(4-Methylphenoxy)pentyl]aminoquinazoline
m.p. 128°~130° C.

4-(6-Phenoxyhexyl)aminoquinazoline
m.p. 105°~108° C.

4-(7-Phenoxyheptyl)aminoquinazoline
m.p. 83°~86° C.

4-(8-Phenoxyoctyl)aminoquinazoline
m.p. 74°~78° C.

4-[2-(2-n-Propylphenoxy)ethyl]aminoquinazoline
m.p. 74°~78° C.

6-Methyl-4-[4-(2-chlorophenoxy)butyl]aminoquinazoline
m.p. 113°~116° C.

4-[2-(2-Methoxy-4-methylphenoxy)ethyl]aminoquinazoline
m.p. 155°~156° C.

4-[2-(3-Methoxyphenoxy)ethyl]aminoquinazoline
m.p. 165°~166° C.

4-[2-(2-Methoxy-4-chlorophenoxy)ethyl]aminoquinazoline
m.p. 163°~166° C.

4-[2-(2-Methyl-3-chlorophenoxy)ethyl]aminoquinazoline
m.p. 154°~156° C.

2-Methyl-4-(3-phenoxypropyl)aminoquinazoline
m.p. 111°~115° C.

4-[2-(2,5-Dimethoxyphenoxy)ethyl]aminoquinazoline
m.p. 178°~180° C.

4-[2-(3,5-Dimethyl-4-bromophenoxy)ethyl]aminoquinazoline
m.p. 218°~220° C.

4-[2-(2,4-Dichloro-6-methylphenoxy)ethyl]aminoquinazoline
m.p. 165°~167° C.

4-[2-(2-Trifluoromethyl-4-chlorophenoxy)ethyl]aminoquinazoline
m.p. 159°~162° C.

6-Chloro-4-[2-(2-Chlorophenoxy)ethyl]aminoquinazoline
m.p. 176°~178° C.

4-[2-(2-n-Butoxyphenoxy)ethyl]aminoquinazoline
m.p. 89°~92° C.

4-[2-(2-Trifluoromethylphenoxy)ethyl]aminoquinazoline
m.p. 143°~145° C.

4-[2-(4-Bromophenylthio)ethyl]aminoquinazoline
m.p. 162°~163° C.

4-[2-(4-Isopropoxyphenoxy)ethyl]aminoquinazoline
m.p. 148°~151° C.

4-[2-(2,4-Dibromophenoxy)ethyl]aminoquinazoline
m.p. 161°~163° C.

6-Chloro-4-[2-(2,4,6-trichlorophenoxy)ethyl]aminoquinazoline m.p. 185°~187° C.
4-[2-(2,3,6-Trimethylphenoxy)ethyl]aminoquinazoline
m.p. 155°~158° C.
4-[2-(Benzyloxy)ethyl]aminoquinazoline
m.p. 111°~113° C.
4-(3-Phenoxypropyl)aminoquinazoline
m.p. 129°~131° C.
6-Nitro-4-(3-phenoxypropyl)aminoquinazoline
m.p. 121°~123° C.
2-Chloro-4-[3-(4-chlorophenoxy)propyl]aminoquinazoline
m.p. 131°~133° C.
2-Chloro-4-[2,2-dimethyl-2(4-methylphenoxy)ethyl]aminoquinazoline
m.p. 121°~124° C.
4-(5-Phenoxypentyl)aminoquinazoline
m.p. 106°~108° C.
4-[6-(2-Methylphenoxy)hexyl]aminoquinazoline
m.p. 90°~92° C.
4-[7-(2-Methylphenoxy)heptyl]aminoquinazoline
m.p. 88°~91° C.
4-[8-(2-Methylphenoxy)octyl]aminoquinazoline
m.p. 70°~73° C.
4-[12-(2-Methylphenoxy)dodecyl]aminoquinazoline
m.p. 66°~70° C.
4-[2-(2-n-Butylphenoxy)ethyl]aminoquinazoline
m.p. 159°~163° C.
4-[2-(2-tert-Butylphenoxy)ethyl]aminoquinazoline
m.p. 158°~160° C.

The compounds in this invention may be formulated for use with the preparations commonly employed as an agricultural fungicide, for example, powdery dusts, coarse dusts, fine granules, granules, wettable powders, emulsifiable concentrates, aqueous liquids, water soluble powders, oil suspensions and so on, with admixture of a carrier and, if required, other auxiliary agents. The carrier as used herein means a synthetic or natural and inorganic or organic substance that is mixed with an active compound and can assist an active compound in its arrival to the sitis to be treated and make it easy to store, transport or handle.

As suitable solid carriers may be mentioned inorganic substances such as clays, which may be represented by Kaolinite, Montmorillonite or Attapulgite, talc, mica, pyrophyllite, pumice, vermiculite, gypsum, calcium carbonate, dolomite, diatomaceous earth, magnesium carbonate, apatite, zeolite, silicic anhydride, synthetic calcium silicate and the like, vegetable organic substances such as soybean meal, tobacco powder, walnut powder, wheat flour, wood meal, starch, crystalline cellulose and the like, synthetic or natural high polymer compounds such as cumarone resin, petroleum resin, alkyd resin, polyvinyl chloride, polyalkylene glycol, ketone resin, ester gum, copal gum, dammar gum, and the like, waxes such as carnauba wax, beeswax and the like, or urea.

As suitable liquid media or carriers may be mentioned paraffin or naphthene hydrocarbons such as kerosine, mineral oil, spindle oil, white oil and the like, aromatic hydrocarbons such as benzene, toluene, xylene, ethylbenzene, cumene, methylnaphthalene and the like, chlorinated hydrocarbons such as carbon tetra chloride, chloroform, trichloroethylene, monochlorobenzene, o-chlorotoluene and the like, ethers such as dioxane, tetrahydrofuran and the like, ketones such as acetone, methyl ethyl ketone, diisobutylketone, cyclohexanone, acetophenone, isophorone and the like, esters such as ethyl acetate, amyl acetate, ethylene glycol acetate, diethylene glycol acetate, dibutyl maleate, diethyl succinate and the like, alcohols such as methanol, n-hexanol, ethylene glycol, diethylene glycol, cyclohexanol, benzyl alcohol and the like, ether alcohols such as ethylene glycol ethyl ether, ethylene glycol phenyl ether, diethylene glycol ethyl ether, diethylene glycol butyl ether and the like, polar solvents such as dimethylformamide, dimethylsulfoxide and the like, or water.

As the surface active agents used for emulsifying, dispersing, wetting, spreading, binding, controlling disintegration, stabilizing active ingredient, improving fluidity, rust proofing and so on may be utilized any of non-ionic, anionic, cationic and amphoteric ones, but non-ionic and/or anionic agents are usually employed. As suitable non-ionic surface active agents may be mentioned, for example, polymerization adducts of ethylene oxide and higher alcohols such as lauryl alcohol, stearyl alcohol, oleyl alcohol and the like, polymerization adducts of ethylene oxide and alkyl phenols such as isooctyl phenol, nonyl phenol and the like, polymerization adducts of ethylene oxide and alkyl naphthols such as butyl naphthol, octyl naphthol and the like, polymerization adducts of ethylene oxide and higher fatty acids such as palmitic acid, stearic acid, oleic acid and the like, polymerization adducts of ethylene oxide and mono- or di-alkyl phosphoric acids such as stearyl phosphoric acid, dilauryl phosphoric acid and the like, polymerization adducts of ethylene oxide and amines such as dodecyl amine, stearic acid amide and the like, polymerization adducts of ethylene oxide and higher fatty acid esters of polyhydric alcohols such as sorbitan and said fatty acid esters, polymerization adducts of ethylene oxide of propylene oxide and so on. As suitable anionic surface active agents may be mentioned, for example, alkyl sulfate salts such as sodium lauryl sulfate, oleyl sulfate amine salt and the like, alkyl sulfonate salts such as sodium dioctyl sulfosuccinate, sodium 2-ethylhexene sulfonate and the like, aryl sulfonate salts such as sodium isopropylnaphthalene sulfonate, sodium methylenebisnaphthalene sulfonate, sodium ligninsulfonate, sodium dodecylbenzene sulfonate and the like.

Moreover, the agricultural fungicidal compositions of this invention may be used in combination with high molecular compounds or other auxiliary agents such as casein, gelatin, albumin, glue, sodium alginate, carboxymethyl cellulose, methyl cellulose, hydroxyethyl cellulose, polyvinyl alcohol and the like for improving properties and increasing biological effects thereof.

The above-mentioned carriers and various auxiliary agents may be optionally utilized alone or in combination for desired purposes, with consideration for the type of preparation, application and other factors.

Dusts usually contain, for example, 1 to 25 parts by weight of the active compound and the remainder is a solid carrier.

Wettable powders usually contain, for example, 25-90 parts by weight of the active compound and the remainder is a solid carrier and a dispersing and wetting agent, if required, together with a protective colloidal agent, a thixotropic agent, an anti-foaming agent and the like.

Granules usually contain 1-35 parts by weight of the active compound and a major portion of the remainder is a solid carrier. The active compound is homogeneously admixed with the solid carrier or adhered or adsorbed on the carrier surface and the size of a granule is about 0.2-1.5 mm.

Emulsifiable concentrates usually contain, for example, 5–50 parts by weight of the active compound and about 5–20 parts by weight of an emulsifying agent, the remainder being a liquid carrier, if required, together with a corrosive inhibitor.

The fungicidal compositions of this invention which are formulated into various types of preparations as above, may be applied in a paddy or upland field at 1–5000 g, preferably 10–1000 g of the active ingredient per 10 acres, for pre- or post-emergence foliage spraying or soil drenching or spraying onto water to control diseases effectively.

Further, the fungicidal compositions of this invention, when employed for seed disinfection or coating, may effectively control soil-borne or seed infectious diseases by coating seeds at 0.1–2%, preferably 0.2–0.5%, of the active ingredient per weight of the seed.

The fungicidal compositions of this invention may be preferably combined with other fungicides for broader fungicidal spectra and, in some cases, a synergistic effect is expectable.

As examples of such other fungicides may be, for instance, carbamate type fungicides such as 3,3'-ethylene-bis(tetrahydro-4,6-dimethyl-2H-1,3,5-thiadiazine-2-thione; zinc or manganese ethylenebisdithiocarbamate; bis(dimethyldithiocarbamoyl)disulfide; zinc propylenebisdithiocarbamate; bis(dimethyldithiocarbamoyl)ethylenediamine; nickel dimethyldithiocarbamate; methyl 1-(butylcarbamoyl))-2-benzimidazolcarbamate; 1,2-bis(3-methoxycarbonyl-2-thioureido)benzene; phosphorous type fungicides such as O,O-diisopropyl-S-benzylphosphorothioate; O-ethyl-S,S-diphenyldithiophosphate and the like, dicarboximide type fungicides such as N-trichloromethylthio-4-cyclohexene-1,2-dicarboximide; N-tetrachloroethylthio-4-cyclohexene-1,2-dicarboximide and the like, oxazine type fungicides such as 5,6-dihydro-2-methyl-1,4-oxazine-3-carboxanilide-4,4-dioxide; 5,6-dihydro-2-methyl-1,4-oxazine-3-carboxanilide and the like, naphthoquinone type fungicides such as 2,3-dichloro-1,4-naphthoquinone and the like, other fungicides such as pentachloronitrobenzene; 3-hydroxy-5-methylisoxazole; N-(2,3-dichlorophenyl)tetrachlorophthalamic acid; 5-ethoxy-3-trichloromethyl-1,2,4-thiadiazole; 2,4,6-trichloro-6-(o-chloroanilino)-1,3,5-triazine; 2,3-dicyano-1,4-dithioanthraquinone; copper 8-quinolate; Validamycin; cycloheximide; iron methanearsonate; tetrachloroisophthalonitrile; 2-(1-methylpropyl)-4,6-dinitrophenyl β,β-dimethylacrylate; triphenyltinhydroxide; Polyoxin; Phytomycin, Kasugamycin; Blasticidin S; 4,5,6,7-tetrachlorophthalide and the like, but they are not critical.

The fungicidal compositions of the invention may also be applied in a mixture with insecticides as illustratively given below: phosphorus type insecticides such as O,O-diethyl O-(2-isopropyl-4-methyl-6-pyrimidinyl)-phosphorothioate; O,O-diethyl S-2-[(ethylthio)ethyl]-phosphorodithioate; O,O-dimethyl O-(3-methyl-4-nitrophenyl)thiophosphate; O,O-dimethyl S-(N-methyl-carbamoylmethyl)phosphorodithioate; O,O-dimethyl S-(N-methyl-N-formylcarbamoylmethyl)phosphorodithioate; O,O-dimethyl S-2-(ethylthio)ethylphosphorodithioate; O,O-dimethyl-1-hydroxy-2,2,2-trichloroethylphosphonate; O,O-diethyl-O-(5-phenyl-3-isoxazolyl)-phosphorothioate; methyl(4-bromo-2,5-dichlorophenyl)-phenylphosphonothioate; O,O-dimethyl-O-(3-methyl-4-methylmercaptophenyl)thiophosphate; O-ethyl-O-p-cyanophenyl phenylphosphonothioate; O,O-diethyl S-(1,2-dicarboethoxyethyl)-phosphorodithioate; 2-chloro-1-(2,4,5-trichlorophenyl) vinyldimethyl phosphate; 2-chloro-1-(2,4-dichlorophenyl)-vinyldimethyl phosphate; O,O-dimethyl O-p-cyanophenyl phosphorothioate; 2,2-dichlorovinyl dimethyl phosphate; O,O-diethyl O-2,4-dichlorophenyl phosphorothioate; ethyl mercaptophenylacetate O,O-dimethyl phosphorodithioate; S-[(6-chloro-2-oxo-3-benzoxazolinyl)-methyl]O,O-diethylphosphorodithioate; 4-mercaptothiophenyl dipropylphosphate; 2-chloro-1-(2,4-dichlorophenyl)vinyl diethylphosphate; O,O-diethyl-O-(3-oxo-2-phenyl-2H-pyridazin-6-yl)phosphorothioate; O,O-dimethyl S-(1-methyl-2-ethylsulfinyl)-ethyl phosphorothiolate; O,O-dimethyl S-phthalimidomethyl phosphoroditioate; dimethylmethylcarbamoylethylthioethyl thiophosphorothiolate; O,O-diethyl S-(N-ethoxycarbonyl-N-methylcarbamoylmethyl) phosphorodithioate; O,O-dimethyl-S-[2-methoxy-1,3,4-thiadiazol-5(4H)-onyl-(4)-methyl]dithiophosphate; 2-methoxy-4H-1,3,2-benzodioxaphosphorin 2-sulfide; O,O-diethyl-O-(3,5,6-trichloro-2-pyridyl)phosphorothioate; O-ethyl-O-2,4-dichlorophenyl thionobenzene phosphonate; S-[4,6-diamino-S-triazin-2-yl-methyl]-O,O-dimethyl phosphorodithioate; O-ethyl O-p-nitrophenylphenylphosphorothioate; O,S-dimethyl-N-acetyl phosphoroamidothioate or the like; carbamate type insecticides such as 1-naphthyl N-methylcarbamate; S-methyl-N-[methylcarbamoyloxy]thioacetoimidate; m-tolyl methylcarbamate; 3,4-xylyl methylcarbamate; 3,5-xylyl methylcarbamate; 2-sec-butylphenyl-N-methylcarbamate; 2-isopropoxyphenyl-N-methylcarbamate; 1,3-bis(carbamoylthio)-2-(N,N-dimethylamino)propane hydrochloride; and the like, other insecticides such as N,N-dimethyl-N'-(2-methyl-4-chlorophenyl) formamidine hydrochloride, nicotine sulfate, Milbemycin, 6-methyl,2,3-quinoxalinedithiocyclic S,S-dithiocarbonate, 2,4-dinitro-6-sec-butylphenyl dimethylacrylate; 1,1-bis(p-chlorophenyl)-2,2,2-trichloroethanol; 2-(p-tert-butylphenoxy)isopropyl-2'-chloroethylsulfite; azoxybenzene; di-(p-chlorophenyl)-cyclopropyl carbinol; isopropyl-4,4'-dichlorobenzylate; ethyl-4,4'-dichlorobenzylate; or machine oil and the like.

The fungicidal composition of this invention can be used with a controlling agent against rice blast, Helminothosporium leaf spot, bacterial leaf blight, rice stem borer, planthopper and/or leafhopper to save labor. The agricultural chemicals, which may be used with the present fungicidal composition, are as mentioned hereinabove. The combination ratio of these agents may vary depending upon diseases or insects to be controlled and preparation forms to be used, these agents are prepared and applied with an effective amount of active ingredients required for controlling. In particular, dusts and fine granules are preferable for controlling rice plant diseases and soil treatment.

Examples of the agricultural fungicidal composition of this invention will be given below. All parts are given by weight unless otherwise stated.

Formulation 1. Dusts

Five parts of the compound having compound No. 8, 50 parts of talc and 45 parts of kaolin were uniformly mixed to form dusts.

Formulation 2. Wattable powders

Fifty parts of the compound having compound No. 20, 29 parts of clay, 10 parts of diatomaceous earth, 5 parts of white carbon, 3 parts of sodium lignosulfonate, 2 parts of "Newcol" 1106 (trade name, Nihon Nyukazai K.K. Japan) and 1 part of polyvinyl alcohol were uniformly mixed in a mixer and pulverized three times by a hammer mill to give wettable powders.

Formulation 3. Granules

Seventy parts of the compound having compound No. 32 was finely pulverized and 30 parts of clay was added thereto and then mixed in a mixer to form a premixture. 10 parts of the premix was uniformly mixed with 60 parts of clay and 30 parts of bentonite in a mixer. The mixture was kneaded with a suitable amount of water in a kneader, extruded through a screen having a diameter of 0.8 mm and dried in a draft drier at 50° C. The product thus formed was adjusted by a sifter to form granules.

Experimental examples of the present fungicidal compositions thus prepared are given below. The wettable powders prepared according to the procedures in the abovementioned Formulation 2 are used in the following experiments, each containing 50% by weight of the active compound of this invention.

Experiment 1

Test for Effect Against the Rice Blast

Rice plant seedlings, variety Nohrin No. 20, at 4 to 5 leaf stage were sprayed with each test preparation at 500 ppm in a total amount of 30 ml per 2 pots. After 3 days, the rice blast fungi were inoculated into the host plants by spraying a spore suspension of *Piricularia oryzae*, and the host plants were kept in a room for 48 hours under conditions at 20 ° to 22° C. 100% relative humidity. The host plants were then placed in a greenhouse at 24° to 26° C., and after further 3 days the number of diseased spots of the upper two leaves of the host plants was investigated. Each test was conducted at triplicate runs and the damage was indicated by the mean number of diseased spots per leaf.

The results are given in Table 1. None of the active compounds exhibited phototoxicity.

Table 1.

| Test compound No. | Number of diseased spots per leaf | Test compound No. | Number of diseased spots per leaf |
|---|---|---|---|
| 4 | 0.0 | 110 | 1.0 |
| 6 | 0.9 | 111 | 1.0 |
| 9 | 1.0 | 112 | 0.9 |
| 13 | 0.1 | 121 | 0.7 |
| 20 | 1.1 | 122 | 1.2 |
| 21 | 0.8 | 135 | 0.9 |
| 42 | 1.0 | 137 | 0.1 |
| 52 | 1.1 | 141 | 1.4 |
| 55 | 0.9 | 142 | 1.1 |
| 57 | 1.2 | 144 | 1.3 |
| 68 | 0.0 | 159 | 0.0 |
| 93 | 1.0 | 160 | 0.8 |
| 94 | 1.1 | 173 | 0.0 |
| 96 | 1.3 | 179 | 1.2 |
| 98 | 1.0 | 204 | 1.1 |
| 102 | 1.1 | 222 (hydrochloride) | 1.2 |
| 103 | 0.9 | | |
| 109 | 1.5 | | |

Experiment 2

Test for Effect Against the Brown Spot of Rice Plants

Following the procedures of Experiment 1, but using a spore suspension of *Cochliobolus miyabeanus* and test preparations at 500 ppm, the effect against the brown spot was tested. Each test was conducted at triplicate runs and the damage was indicated by the mean number of diseased spots per leaf. The results are given in Table 2. None of the active compounds exhibited any phytotoxicity.

Table 2.

| Test compound No. | Number of diseased spots per leaf |
|---|---|
| 2 | 0.0 |
| 4 | 2.0 |
| 6 | 0.0 |
| 135 | 0.0 |
| 222 (hydrochloride) | 3.2 |

Experiment 3

Test for Effect Against the Bacterial Leaf Blight of Rice Plants

Groups of rice plants, variety Kimmaze, were planted in a series of Wager pots having a surface area of 1/5000 are and grown to the flag leaf stage. Each rice plant was inoculated with a suspension of pathogenic microorganism *Xanthomonas oryzae* by spraying and then kept for 1 day in a room at 26° to 28° C., 100% relative humidity. The pots were placed in a greenhouse at 28° C. Three days after the inoculation, each pot was treated with 20 ml of an aqueous suspension containing 1000 ppm of one of the active compounds shown in Table 3, applied to the host plants by spraying over their stems and leaves. 20 days after the application of the active compounds, the diseased area percentage of the flag and second leaves was measured. Three pots were used for each test. The results are given in Table 3. Compounds No. 43 and No. 55 showed slight phytotoxicity.

Table 3.

| Test compound No. | Diseased area (%) | Test compound No. | Diseased area (%) |
|---|---|---|---|
| 3 | 17 | 95 | 14 |
| 10 | 15 | 102 | 18 |
| 11 | 5 | 106 | 0 |
| 12 | 21 | 107 | 0 |
| 13 | 9 | 109 | 13 |
| 18 | 10 | 111 | 7 |
| 20 | 8 | 121 | 3 |
| 24 | 12 | 136 | 0 |
| 40 | 0 | 139 | 6 |
| 42 | 10 | 140 | 11 |
| 43 | 14 | 147 | 7 |
| 52 | 6 | 153 | 13 |
| 54 | 9 | 162 | 0 |
| 55 | 15 | 171 | 4 |
| 57 | 9 | 172 | 7 |
| 65 | 10 | 173 | 16 |
| 79 | 20 | 175 | 8 |
| 84 | 15 | 179 | 5 |
| 87 | 12 | 204 | 14 |
| 88 | 0 | 206 | 11 |
| 93 | 9 | 285 | 10 |

Experiment 4

Test for Effect Against the Late Blight of Tomatoes

Groups of tomatoes, variety Shinfukuju, at the 5 to 6 leaf stage were sprayed with 20 ml per pot of an aqueous suspension containing 500 ppm of one of the active compounds shown in Table 4. After air-drying, each plant was inoculated with a spore suspension of pathogenic microorganism *Phytophthora infestans* by spraying and kept for 24 hours in a wet room at 20° C. and more than 95% humidity. The pots were then kept in a greenhouse at 25° C., and after 5 days, the diseased area of the upper three leaves of each plant was measured. Two pots were used for each test and the average diseased area per leaf was calculated. The results are given in Table 4. None of the active compounds exhibited any phytotoxicity.

Table 4.

| Test compound No. | Diseased area (%) | Test compound No. | Diseased area (%) | Test compound No. | Diseased area (%) |
|---|---|---|---|---|---|
| 3 | 15 | 102 | 0 | 172 | 2 |
| 4 | 0 | 103 | 0 | 173 | 0 |
| 8 | 9 | 105 | 28 | 174 | 0 |
| 9 | 10 | 106 | 0 | 175 | 0 |
| 10 | 26 | | | | |
| 13 | 0 | | | | |
| 14 | 11 | 107 | 0 | 179 | 16 |
| 20 | 2 | 109 | 0 | 195 | 0 |
| 21 | 16 | 110 | 0 | 197 | 1 |
| 22 | 15 | 111 | 0 | 198 | 0 |
| 23 | 15 | 112 | 0 | 199 | 0 |
| 24 | 0 | 113 | 0 | 200 | 0 |
| 27 | 3 | 114 | 2 | 201 | 0 |
| 28 | 4 | 115 | 0 | 202 | 2 |
| 30 | 2 | 117 | 0 | 204 | 0 |
| 31 | 0 | 118 | 0 | 206 | 2 |
| 33 | 15 | 121 | 0 | 222 | 0 |
| 34 | 34 | 122 | 4 | 223 | 16 |
| 37 | 17 | 124 | 0 | 225 | 7 |
| 40 | 0 | 125 | 7 | 226 | 13 |
| 41 | 5 | 126 | 0 | 229 | 3 |
| 42 | 20 | 127 | 4 | 232 | 5 |
| 43 | 24 | 128 | 0 | 235 | 0 |
| 46 | 1 | 129 | 0 | 248 | 1 |
| 48 | 0 | 137 | 18 | 261 | 0 |
| 51 | 0 | 139 | 4 | 285 | 8 |
| 55 | 9 | 140 | 18 | 286 | 12 |
| 56 | 16 | 141 | 22 | 287 | 4 |
| 57 | 27 | 142 | 23 | 291 | 10 |
| 59 | 0 | 144 | 11 | 292 | 9 |
| 62 | 0 | 151 | 28 | 294 | 16 |
| 64 | 5 | 152 | 13 | 295 | 5 |
| 65 | 3 | 153 | 16 | | |
| 73 | 3 | 154 | 5 | | |
| 76 | 23 | 155 | 0 | | |
| 79 | 21 | 157 | 0 | | |
| 84 | 0 | 158 | 15 | | |
| 87 | 0 | 159 | 0 | | |
| | | 164 | 27 | | |
| | | 170 | 0 | | |

Experiment 5

Test for Effect Against the Early Blight of Tomatoes

Groups of two tomato plants, variety Shinfukuju, were planted in a series of Wager pots having a diameter of 12 cm and used as host plants when at the 5 to 6 leaf stage. Each pot was treated with 30 ml of an aqueous suspension containing 500 ppm of one of the active compounds shown in Table 5, applied to the host plants by spraying over their stems and leaves. After air-drying, each plant was inoculated with a spore suspension of the pathogenic microorganism *Alternalia solani* and kept in a wet room for 24 hours at 20°–22° C., 100% relative humidity. The pots were then placed in a greenhouse for 3 days. The presence of the disease of all leaves was investigated and the number of disease spots per leaf was calculated, using three pots for each test. The results are given in Table 5. None of the active compounds exhibited any phytotoxicity.

Table 5.

| Test compound No. | Number of diseased spots per leaf | Test compound No. | Number of diseased spots per leaf |
|---|---|---|---|
| 6 | 16 | 125 | 3 |
| 14 | 0 | 127 | 6 |
| 20 | 0 | 131 | 7 |
| 21 | 37 | 142 | 25 |
| 30 | 5 | 144 | 20 |
| 32 | 25 | 151 | 19 |
| 39 | 9 | 152 | 3 |
| 42 | 10 | 153 | 2 |
| 47 | 0 | 157 | 0 |
| 49 | 0 | 158 | 14 |
| 53 | 20 | 159 | 0 |
| 55 | 32 | 160 | 0 |
| 65 | 2 | 170 | 16 |
| 68 | 0 | 172 | 0 |
| 71 | 6 | 173 | 20 |
| 73 | 12 | 175 | 0 |
| 87 | 25 | 177 | 0 |
| 94 | 49 | 183 | 4 |
| 96 | 13 | 195 | 0 |
| 97 | 0 | 197 | 14 |
| 98 | 0 | 198 | 0 |
| 102 | 0 | 200 | 27 |
| 103 | 29 | 202 | 10 |
| 104 | 0 | 204 | 0 |
| 106 | 14 | 206 | 0 |
| 109 | 18 | 222 | |
| 110 | 0 | (hydrochloride) | 0 |
| 111 | 7 | 223 | 10 |
| 113 | 6 | 225 | 18 |
| 117 | 12 | 232 | 9 |
| 118 | 34 | 235 | 0 |
| 120 | 27 | 285 | 7 |
| 122 | 16 | 286 | 7 |
| 124 | 23 | 287 | 7 |
| | | 291 | 3 |
| | | 295 | 7 |

Experiment 6

Test for Effect Against the Anthracnose of Cucumbers

Groups of two cucumber plants, variety Sagamihanshiro, were planted in a series of Wagner pots having a diameter of 12 cm and used as host plants when the first leaf was fully grown and open. Each test group of three pots was treated with one of the active compounds shown in Table 6, by spraying on an aqueous suspension containing 500 ppm of the active compound at the rate of 30 ml per 3 pots. After air-drying, the host plants were inoculated by spraying with a spore suspension of the pathogenic microorganism *Colletotrichum lagenarium* and kept in a wet room for 24 hours at 20° to 22° C., 100% relative humidity. The pots were then placed in a greenhouse at 26° C., and seven days after the inoculation, the diseased area percentage of the cotyledon and the first leaf was calculated. The results are given in Table 6.

None of the active compounds exhibited any phytotoxicity.

Table 6.

| Test compound No. | Diseased area (%) | Test compound No. | Diseased area (%) | Test compound No. | Diseased area (%) |
|---|---|---|---|---|---|
| 2 | 14 | 103 | 0 | 158 | 16 |
| 4 | 6 | 106 | 0 | 159 | 0 |
| 6 | 0 | 107 | 0 | 170 | 0 |
| 8 | 0 | 109 | 0 | 172 | 0 |
| 13 | 0 | 110 | 0 | 173 | 0 |
| 20 | 5 | 112 | 3 | 174 | 0 |

Table 6.-continued

| Test compound No. | Diseased area (%) | Test compound No. | Diseased area (%) | Test compound No. | Diseased area (%) |
| --- | --- | --- | --- | --- | --- |
| 23 | 0 | 113 | 0 | 175 | 21 |
| 28 | 2 | 114 | 0 | 179 | 2 |
| 30 | 0 | | | | |
| 35 | 0 | 117 | 5 | 197 | 0 |
| 39 | 11 | 118 | 0 | 200 | 2 |
| 41 | 0 | 119 | 13 | 201 | 0 |
| 42 | 20 | 122 | 0 | 204 | 1 |
| 46 | 5 | 124 | 0 | 222 | 0 |
| 47 | 13 | 125 | 0 | 223 | 3 |
| 48 | 0 | 126 | 0 | 225 | 10 |
| 51 | 0 | 127 | 4 | 226 | 0 |
| 55 | 8 | 128 | 6 | 229 | 5 |
| 57 | 17 | 129 | 0 | 232 | 31 |
| 59 | 12 | 136 | 19 | 234 | 0 |
| 62 | 0 | 137 | 0 | 248 | 12 |
| 65 | 0 | 141 | 0 | 261 | 7 |
| 68 | 0 | 142 | 15 | 285 | 11 |
| 70 | 0 | 144 | 0 | 286 | 2 |
| 79 | 0 | 147 | 12 | 287 | 0 |
| 84 | 12 | 152 | 9 | 288 | 2 |
| 85 | 8 | 153 | 9 | 290 | 0 |
| 102 | 0 | 155 | 6 | 291 | 0 |
| | | | | 295 | 2 |

Experiment 7

Test for Effect Against the Powdery Mildew of Cucumbers

Cucumber seedlings, variety Sagamihanshiro, planted two per 12 cm diameter pot, were used as host plants at the stage when the first leaf was fully grown and open. Each test group of three pots was treated with one of the active compounds shown in Table 7, by spraying on an aqueous suspension containing 500 ppm of the active compound at the rate of 20 ml per 3 pots. After air-drying, the host plants were inoculated with *Sphaerotheca fuliginea* by brushing already infected cucumber leaves with a small brush and letting the microorganism fall onto the host plants. The inoculated plants were kept in a greenhouse at 24° to 26° C. for 10 days, and at the end of this period the diseased area percentage was measured. Three pots were used for each test. The results are given in Table 7. None of the active compounds exhibited any phytotoxicity.

Table 7.

| Test compound No. | Diseased area (%) | Test compound No. | Diseased area (%) | Test compound No. | Diseased area (%) |
| --- | --- | --- | --- | --- | --- |
| 6 | 18 | 70 | 5 | 147 | 8 |
| 8 | 0 | 71 | 13 | 154 | 8 |
| 13 | 0 | 79 | 2 | 163 | 13 |
| 14 | 3 | 84 | 0 | 170 | 7 |
| 20 | 0 | 85 | 0 | 171 | 10 |
| 23 | 7 | 102 | 5 | 173 | 0 |
| 24 | 30 | 103 | 19 | 174 | 0 |
| 27 | 0 | 106 | 0 | 175 | 15 |
| 28 | 2 | 107 | 0 | 179 | 3 |
| 30 | 0 | 110 | 8 | 195 | 4 |
| 31 | 0 | 111 | 13 | 197 | 3 |
| 35 | 0 | 113 | 4 | 204 | 7 |
| 37 | 3 | 114 | 0 | 206 | 0 |
| 39 | 6 | 118 | 28 | 222 | 0 |
| 40 | 9 | 120 | 20 | (hydrochloride) | |
| 41 | 0 | 124 | 4 | 225 | 0 |
| 43 | 0 | 126 | 18 | 226 | 3 |
| 46 | 0 | 127 | 8 | 232 | 0 |
| 47 | 11 | 128 | 18 | 234 | 0 |
| 55 | 2 | | | | |

Table 7.-continued

| Test compound No. | Diseased area (%) | Test compound No. | Diseased area (%) | Test compound No. | Diseased area (%) |
| --- | --- | --- | --- | --- | --- |
| 56 | 4 | | | | |
| 57 | 17 | 129 | 7 | 248 | 8 |
| 59 | 23 | 135 | 0 | 261 | 5 |
| 62 | 0 | 137 | 0 | 286 | 0 |
| 64 | 10 | 142 | 10 | 287 | 10 |
| 65 | 0 | 142 | 12 | 288 | 6 |
| 67 | 5 | 144 | 12 | 290 | 3 |
| | | | | 295 | 3 |

Experiment 8

Test for Repellent Action Against the Fourth Instar Larva of Cabbage Armyworms Cabbage leaves were dipped for 30 seconds in an aqueous suspension containing 1000 ppm or 100 ppm of one of the active compounds shown in Table 8. After air-drying, the leaves were placed on vermiculite in a plastic receptacle of 15 cm×20 cm, and five per receptacle of the fourth instar larvae of cabbage armyworm were released on the leaves, while other leaves without dipping being placed 12 cm away from the dipped leaves in the receptacle.

After 24 hours, the extent of ingestion of the dipped and non-dipped leaves was measured, using two receptacles for each test.

The results are given in Table 8.

Table 8.

| Test compound No. | Extent of ingestion | | | |
| --- | --- | --- | --- | --- |
| | 1000 ppm | | 100 ppm | |
| | Dipped | Non-dipped | Dipped | Non-dipped |
| 8 | — | +++ | ± | +++ |
| 41 | — | +++ | ± | +++ |
| Control (None) | | +++ | | +++ |

Experiment 9

Test for Repellent Action Against the Third Instar Larva of Tobacco Cutworm

Cabbage leaves were dipped for 30 seconds in an aqueous suspension containing 1000 ppm or 100 ppm of one of the active compounds shown in Table 9. After air-drying, the leaves were placed in a plastic receptacle having a diameter of 8 cm, and 10 per receptacle of the third instar larvae of tobacco cutworm were released on the leaves. After 72 hours, the extent of ingestion of the leaves was measured, using two receptacles for each test. The results are given in Table 9.

Table 9.

| Test compound No. | Extent of ingestion | |
| --- | --- | --- |
| | 1000 ppm | 100 ppm |
| 62 | — | — |
| 102 | ± | + |
| 113 | — | ± |
| 118 | ± | + |
| 126 | — | ± |
| 128 | — | ± |
| Control (None) | +++ | +++ |

What is claimed is:

1. A method for protecting plants from fungicidal attack comprising applying to the site of said plants an agricultural fungicidal composition which contains as an active ingredient a fungicidally effective amount of a compound having the formula

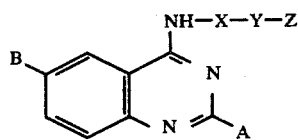

wherein:
A and B are same or different and each represents a hydrogen atom, a lower alkyl group, a halogen atom or a nitro group;
X represents an alkylene group;
Y represents an oxygen atom or a sulfur atom; and
Z represents an alkyl group, an aralkyl group, a naphthyl group, an unsubstituted phenyl group or a phenyl group substituted with 1 to 3 substituents which are same or different and are selected from the group consisting of a lower alkyl group, a lower alkoxy group, a lower alkylthio group, a phenyl group, a trifluoromethyl group and a halogen atom; or a salt thereof;
and an agriculturally acceptable carrier.

2. The method of claim 1 wherein A and B are same or different and each represents a hydrogen atom, a methyl group, a chlorine atom or a nitro group.

3. The method of claim 1 wherein A is a hydrogen atom or a chlorine atom and B is a hydrogen atom, methyl group, a chlorine atom or a nitro group.

4. The method of claim 1 wherein both A and B are hydrogen atoms.

5. The method of claim 1 wherein X is a straight or branched chain alkylene group having 2 to 8 carbon atoms.

6. The method of claim 1 wherein Z is a straight or branched chain alkyl group having 1 to 8 carbon atoms, a benzyl group, a naphthyl group, an unsubstituted phenyl group or a phenyl group substituted with 1 to 3 substituents which are same or different and are selected from an alkyl having 1 to 4 carbon atoms, an alkoxy having 1 to 4 carbon atoms, an alkylthio having 1 to 4 carbon atoms, a phenyl, a trifluoromethyl and a halogen.

7. The method of claim 1 wherein Z is an unsubstituted phenyl group or a phenyl group substituted with 1 to 3 substituents which are same or different and are selected from the group consisting of a methyl, methoxy, ethoxy, methylthio, trifluoromethyl and chlorine.

8. The method of claim 1 wherein Z is an unsubstituted phenyl group or a phenyl group substituted with a methyl, methoxy, ethoxy or chlorine.

9. The method of claim 1 wherein A is a hydrogen atom or a chlorine atom, B is a hydrogen atom, a methyl group, a chlorine atom or a nitro group, X is a straight or branched chain alkylene group having 2 to 8 carbon atoms and Z is an unsubstituted phenyl group or a phenyl group substituted with 1 to 3 substituents which are same or different and are selected from the group consisting of a methyl, methoxy, ethoxy, methylthio and chlorine.

10. The method of claim 1 wherein both A and B are hydrogen atoms, X is a straight or branched chain alkylene group having 2 to 8 carbon atoms and Z is an unsubstituted phenyl group or a phenyl group substituted with a methyl, methoxy, ethoxy or chlorine.

11. The method of claim 1 wherein both A and B are hydrogen atoms, X is a straight or branched chain alkylene group having 2 to 8 carbon atoms, Y is an oxygen atom and Z is an unsubstituted phenyl group or a phenyl group substituted with a methyl, methoxy, ethoxy or chlorine.

12. The method of each of claims 1 through 4, wherein X is a straight or branched chain alkylene group having 2 to 8 carbon atoms.

13. The method of claim 12, wherein Z is an unsubstituted phenyl group or a phenyl group substituted with a methyl, methoxy, ethoxy or chlorine.

14. The method of claim 1 wherein said active ingredient is 4-[2-(2-chlorophenoxy)ethyl]aminoquinazoline.

15. The method of claim 1 wherein said active ingredient is 4-[2-(2-methylphenoxy)ethyl]aminoquinazoline.

16. The method of claim 1 wherein said active ingredient is 4-[2-(2-ethylphenoxy)ethyl]aminoquinazoline.

17. The method of claim 1 wherein said active ingredient is 4-[2-(2-isopropylphenoxy)ethyl]aminoquinazoline.

18. The method of claim 1 wherein said active ingredient is 4-[2-(2-sec-butylphenoxy)ethyl]aminoquinazoline.

19. The method of claim 1 wherein said active ingredient is 4-[2-(2-trifluoromethylphenoxy)ethyl]aminoquinazoline.

20. The method of claim 1 wherein said active ingredient is 4-[2-(4-methylphenoxy)ethyl]aminoquinazoline.

21. The method of claim 1 wherein said active ingredient is 4-[2-(2-methyl-4-chlorophenoxy)ethyl]aminoquinazoline.

22. The method of claim 1 wherein said active ingredient is 4-[2-(2,4-dimethylphenoxy)ethyl]aminoquinazoline.

23. The method of claim 1 wherein said active ingredient is 6-chloro-4-[2-(2,5-dimethylphenoxy)ethyl]aminoquinazoline.

24. The method of claim 1 wherein said active ingredient is 4-[3-(2-methylphenoxy)propyl]aminoquinazoline.

25. The method of claim 1 wherein said active ingredient is 4-[2-methyl-2-(2-methylphenoxy)ethyl]aminoquinazoline.

26. The method of claim 1 wherein said active ingredient is 4-[4-(2-methylphenoxy)butyl]aminoquinazoline.

27. The method of claim 1 wherein said active ingredient is 4-[1,1-dimethyl-2-(2-methylphenoxy)ethyl]aminoquinazoline.

28. The method of claim 1 wherein said active ingredient is 4-[5-(2-methylphenoxy)pentyl]aminoquinazoline.

29. The method of claim 1 wherein said active ingredient is 4-[6-(2-methylphenoxy)hexyl]aminoquinazoline.

30. The method of claim 1 wherein said active ingredient is 4-[7-(2-methylphenoxy)heptyl]aminoquinazoline.

31. The method of claim 1 wherein said active ingredient is 4-[8-(2-methylphenoxy)octyl]aminoquinazoline.

32. The method of claim 1 wherein said active ingredient is 4-[2-(2-n-propylphenoxy)ethyl]aminoquinazoline.

33. The method of claim 1 wherein said active ingredient is 4-[2-(2-n-butylphenoxy)ethyl]aminoquinazoline.

* * * * *

UNITED STATES PATENT AND TRADEMARK OFFICE
CERTIFICATE OF CORRECTION

PATENT NO. : 4,213,987
DATED : July 22, 1980
INVENTOR(S) : Kazuto Nakagami et al It is certified that error appears in the above-identified patent and that said Letters Patent is hereby corrected as shown below:

Column 1, line 55, "gainst" should read -- against --.

Column 28, (Table 7-continued), third column (Test compound No. in the fourth line of said column, (below "137"), replace "142" with -- 141 --.

Signed and Sealed this

Fifth Day of July 1983

[SEAL]

Attest:

GERALD J. MOSSINGHOFF

Attesting Officer          Commissioner of Patents and Trademarks